(12) United States Patent
Gaston et al.

(10) Patent No.: US 11,051,804 B2
(45) Date of Patent: Jul. 6, 2021

(54) ORTHOPEDIC FIXATION SYSTEM AND METHOD OF USE THEREOF

(71) Applicant: DePuy Synthes Products, Inc., Raynham, MA (US)

(72) Inventors: Glenn Gaston, Charlotte, NC (US); Daniel F. Cheney, San Antonio, TX (US); Joseph P. Ritz, Castroville, TX (US); Eric A. Marcano, San Antonio, TX (US); Luke A. Perkins, San Antonio, TX (US); Diana M. Castillo Sanchez, Stoughton, MA (US)

(73) Assignee: Depuy Synthes Products, Inc., Raynham, MA (US)

( * ) Notice: Subject to any disclaimer, the term of this patent is extended or adjusted under 35 U.S.C. 154(b) by 209 days.

(21) Appl. No.: 16/451,652

(22) Filed: Jun. 25, 2019

(65) Prior Publication Data
US 2020/0000464 A1 Jan. 2, 2020

Related U.S. Application Data

(60) Provisional application No. 62/693,015, filed on Jul. 2, 2018.

(51) Int. Cl.
*A61B 17/064* (2006.01)
*A61B 17/17* (2006.01)
*A61B 17/10* (2006.01)
*A61B 17/16* (2006.01)
*A61B 90/00* (2016.01)
*A61B 17/88* (2006.01)
(Continued)

(52) U.S. Cl.
CPC ........ *A61B 17/0642* (2013.01); *A61B 17/064* (2013.01); *A61B 17/10* (2013.01);
(Continued)

(58) Field of Classification Search
CPC ..... A61B 17/0642; A61B 17/10; A61B 17/17; A61B 17/064; A61F 2/441
See application file for complete search history.

(56) References Cited

U.S. PATENT DOCUMENTS

| 8,177,822 B2* | 5/2012 | Medoff | A61B 17/809 606/297 |
| 8,414,594 B2* | 4/2013 | Berger | A61B 17/1728 606/104 |
| 2002/0077701 A1* | 6/2002 | Kuslich | A61F 2/442 623/17.12 |

(Continued)

FOREIGN PATENT DOCUMENTS

EP 3284443 A1 2/2018

OTHER PUBLICATIONS

International Search Report Form PCT/ISA/210 for PCT/IB2019/055508—PCT Application corresponding to U.S. Appl. No. 16/451,652.

*Primary Examiner* — Christian A Sevilla
(74) *Attorney, Agent, or Firm* — Christopher L. Makay

(57) ABSTRACT

An orthopedic fixation system fuses bone, bones, or bone pieces in a predetermined anatomical position. The orthopedic fixation system includes an implant that transitions between an unconstrained shape and a constrained insertion shape, a drill guide, first and second K-wires, and a cannulated drill bit. The drill guide and the first and second K-wires retain the bone, bones, or bone pieces in an anatomical position corresponding with the predetermined anatomical position. The cannulated drill bit fits over the first and second K-wires and drills, respectively, first and second drilled holes into the bone, bones, or bone pieces. After insertion of the implant into the first and second drilled holes, the implant attempts to transition from its constrained insertion shape to its unconstrained shape such that the implant continuously compresses the bone, bones, or bone pieces thereby holding the bone, bones, or bone pieces in the predetermined anatomical position.

27 Claims, 9 Drawing Sheets

(51) Int. Cl.
*A61B 17/68* (2006.01)
*A61B 17/90* (2006.01)

(52) U.S. Cl.
CPC .......... *A61B 17/1637* (2013.01); *A61B 17/17* (2013.01); *A61B 17/1796* (2013.01); *A61B 17/8897* (2013.01); *A61B 2017/681* (2013.01); *A61B 2017/90* (2013.01); *A61B 2090/062* (2016.02)

(56) References Cited

U.S. PATENT DOCUMENTS

| | | | | |
|---|---|---|---|---|
| 2003/0032963 A1* | 2/2003 | Reiss | ............ | A61B 10/025 606/90 |
| 2005/0261781 A1* | 11/2005 | Sennett | ............ | A61B 17/7098 623/23.54 |
| 2008/0210738 A1* | 9/2008 | Shelton | ............ | A61B 17/0644 227/176.1 |
| 2010/0187285 A1* | 7/2010 | Harris | ............ | A61B 17/064 227/179.1 |
| 2013/0206815 A1* | 8/2013 | Fox | ............ | A61B 17/0644 227/176.1 |
| 2013/0213843 A1 | 8/2013 | Knight et al. | | |
| 2016/0074037 A1* | 3/2016 | Cheney | ............ | A61B 17/0684 227/175.1 |
| 2017/0007305 A1* | 1/2017 | Hollis | ............ | A61B 17/1728 |
| 2017/0281157 A1 | 10/2017 | Hartdegen et al. | | |
| 2017/0296174 A1 | 10/2017 | Wahl et al. | | |
| 2020/0000465 A1* | 1/2020 | Maclure | ............ | A61B 17/0642 |

\* cited by examiner

US 11,051,804 B2

ORTHOPEDIC FIXATION SYSTEM AND METHOD OF USE THEREOF

BACKGROUND OF THE INVENTION

1. Field of the Invention

The present invention relates to orthopedic fixation of bone, bones, or bone pieces, and, more particularly, but not by way of limitation, to an orthopedic fixation system and a method of use thereof.

2. Description of the Related Art

Orthopedic fixation often involves implantation of an implant, such as an orthopedic staple, into bone, bones, or bone pieces. The implant, which typically is formed from a shape memory or superelastic material (e.g., Nitinol), includes a natural unconstrained shape and further deforms to store energy and transition to an insertion shape. The implant inserts into the bone, bones, or bone pieces in its insertion shape. Once implanted, the implant attempts to transition from its insertion shape to its unconstrained shape, thereby delivering its stored energy and creating a compression that assists in healing the bone, bones, or bone pieces.

In order to insert an implant into bone, bones, or bone pieces, a surgeon aligns the bone, bones, or bone pieces at a desired orientation necessary for the proper healing thereof. The surgeon then drills holes in the bone, bones, or bone pieces at a desired location and spacing for insertion of the implant when the implant resides in its insertion shape. The surgeon next inserts the implant into the bone, bones, or bone pieces using the pre-drilled holes. With the implant inserted into the bone, bones, or bone pieces, the implant attempts to transition from its insertion shape to its unconstrained shape such that the implant through its continuous compression of the bone, bones, or bone pieces remains implanted in the bone, bones, or bone pieces while holding the bone, bones, or bone pieces in the desired orientation for proper healing thereof.

A very important condition for the proper implantation of an implant into bone, bones, or bone pieces involves the surgeon maintaining the desired orientation of the bone, bones, or bone pieces during the drilling of holes therein. Failure to achieve the desired orientation during the drilling of holes causes inadequate placement of the implant in the bone, bones, or bone pieces such that optimal fixation thereof is not achieved. Presently, the surgeon manually holds the bone, bones, or bone pieces during the drilling of holes therein. While manual holding provides acceptable results, a precise desired orientation of the bone, bones, or bone pieces is difficult to achieve, particularly, when the bone, bones, or bone pieces are small.

Accordingly, an orthopedic fixation system and a method of use thereof that facilitates a precise desired orientation of bone, bones, or bone pieces during insertion of an implant therein will overcome the disadvantages currently experienced during implant surgeries.

SUMMARY OF THE INVENTION

In accordance with the present invention, an orthopedic fixation system facilitates fusion between bone, bones, or bone pieces in a predetermined anatomical position. The orthopedic fixation system includes one or more implants and one or more mechanical constraints, such as an implant insertion device. The orthopedic fixation system further includes instruments, such as one or more drill guides, one or more K-wires, a cannulated drill bit, and optionally a sizing guide, one or more K-wire guides, one or more locating pins, a depth gauge, and a tamp.

The one or more implants include an unconstrained shape and a constrained insertion shape and transition therebetween such that each implant delivers continuous compression to bone, bones, or bone pieces, and, by way of example, to a first bone and a second bone. The one or more implants each include a first leg and a second leg with a bridge therebetween. The first and second legs are spaced apart at a first distance when the implant resides in its unconstrained shape, whereby the first distance of each implant is different. The first and second legs are spaced apart at a second distance when the implant resides in its constrained insertion shape, whereby the second distance of each implant is different. Each implant insertion device from the one or more implant insertion devices constrains an implant from the one or more implants in its constrained insertion shape.

The one or more drill guides each include a first aperture and a second aperture therethrough that are spaced apart a preset distance. The preset distance between the first and second apertures of each drill guide corresponds with the second distance between the first and second legs of one of the implants in its constrained insertion shape. Each drill guide is placeable atop the first bone and the second bone across a fusion site thereof such that the first aperture of the drill guide is located at the first bone and the second aperture of the drill guide is located across the fusion site at the second bone. The one or more drill guides provide for a selection therebetween of a drill guide having a correct size in that its preset distance between the first and second apertures spaces apart the first and second apertures across the fusion site of the first bone and the second bone a desired distance for implantation of one of the implants into the first bone and the second bone.

A first K-wire from the one or more K-wires inserts through a first aperture of a selected drill guide and into the first bone. The first K-wire and the selected drill guide hold the first bone and the second bone such that manipulation of the selected drill guide leverages the first bone and the second bone into a conforming anatomical position corresponding with the predetermined anatomical position. A second K-wire from the one or more K-wires inserts through a second aperture of the selected drill guide and into the second bone such that the first and second K-wires and the drill guide hold the first bone and the second bone in a retained anatomical position that corresponds with the predetermined anatomical position.

The cannulated drill bit via a cannulation thereof fits over the first K-wire and drills into the first bone until the cannulated drill bit creates a first drilled hole. Likewise, the cannulated drill bit fits over the second K-wire and drills into the second bone until the cannulated drill bit creates a second drilled hole. An implant insertion device of the one or more implant insertion devices constraining a selected implant in its constrained insertion inserts the first leg of the selected implant into the first drilled hole and the second leg of the selected implant into the second drilled hole. After release of the selected implant from the implant insertion device, the selected implant attempts to transition from its constrained insertion shape to its unconstrained shape such that the implant continuously compresses the first bone and the second bone thereby holding the first bone and the second bone in the predetermined anatomical position.

A first K-wire guide of the one or more K-wire guides optionally engages a selected drill guide at its first aperture prior to the insertion of the first K-wire into the first bone. The first K-wire guide includes a cannulation sized to receive the first K-wire therethrough such that the first K-wire guide stabilizes the first K-wire within the first aperture of the selected drill guide. The first K-wire guide is removed from over the first K-wire prior to the drilling of the first drill hole using the cannulated drill bit. Similarly, a second K-wire guide optionally engages the selected drill guide at its second aperture prior to the insertion of the second K-wire into the second bone. The second K-wire guide includes a cannulation sized to receive the second K-wire therethrough such that the second K-wire guide stabilizes the second K-wire within the second aperture of the selected drill guide. The second K-wire guide is removed from over the second K-wire prior to the drilling of the second drill hole using the cannulated drill bit.

The sizing guide includes a body that defines at a perimeter thereof a plurality of fixed distances corresponding with the second distance between the first leg and the second leg of the one of the implants in its constrained insertion shape. The plurality of fixed distances for the sizing guide further correspond with the preset distance between the first aperture and the second aperture of one of the drill guides. The sizing guide permits selection of an implant from the one or more implants by indicating a desired distance across the first bone and the second bone for implantation of an implant into the first bone and the second bone.

A first locating pin of the one or more locating pins optionally, after drilling of the first drilled hole and removal of the first K-wire, inserts through the first aperture of the selected drill guide and into the first drilled hole of the first bone to locate the first drilled hole. Likewise, a second locating pin optionally, after drilling of the second drilled hole and removal of the second K-wire, inserts through the second aperture of the selected drill guide and into the second drilled hole of the second bone to locate the second drilled hole. The first and second locating pins locate the first and second drilled holes in the first and second bones after removal of the selected drill guide from over the first and second locating pins.

The depth gauge is used to determine depth of the first and second drilled holes such that an implant with first and second legs having a length corresponding with the depth of the first and second drilled holes may be selected from the one or more implants.

The tamp allows tamping of a selected implant to an implanted position whereby the first leg resides within the first drilled hole, the second leg resides in the second drilled hole, and the bridge abuts the first bone and the second bone across the fusion site thereof.

The orthopedic fixation system is used as follows to fuse bone, bones, or bone pieces, and, by way of example, a first bone and a second bone. A drill guide is selected once a predetermined anatomical position for the first bone and the second bone is determined. The drill guide is placed atop the first bone and the second bone such that the drill guide spans a fusion site of the first bone and the second bone, whereby the first aperture of the drill guide is located at the first bone and the second aperture of the drill guide is located across the fusion site at the second bone. After inserting a first K-wire through the first aperture of the drill guide and into the first bone, a manipulation of the drill guide leverages the first bone and the second bone into a conforming anatomical position followed by a determination of whether the drill guide is a correct size. The drill guide is a correct size when the preset distance between the first aperture and the second aperture spaces apart the first and second apertures across the fusion site of the first bone and the second bone a desired distance for implantation of an implant into the first bone and the second bone. When the drill guide is an incorrect size, the first K-wire is removed from the first aperture of the drill guide along with the drill guide from atop the first bone and the second bone. A different drill guide is selected and utilized with the first K-wire as previously described to leverage the first bone and the second bone into a conforming anatomical position followed by a determination of whether the different drill guide is a correct size. Different drill guides are sequentially selected until a correctly sized drill guide is established. Upon the selection of a correctly sized drill guide, the selected drill guide and the first K-wire hold the first bone and the second bone in a conforming anatomical position while a verification of whether the conforming anatomical position corresponds with the predetermined anatomical position is performed. When the conforming anatomical position does not correspond with the predetermined anatomical position, the first K-wire is removed from the first aperture of the drill guide along with the drill guide from atop the first bone and the second bone. The selected drill guide and the first K-wire as previously described are again employed to leverage and hold the first bone and the second bone in a conforming anatomical position while a verification of whether the conforming anatomical position corresponds with the predetermined anatomical position is performed. The first bone and the second bone are repeatedly manipulated into a conforming anatomical position using the selected drill guide and the first K-wire until the conforming anatomical position corresponds with the predetermined anatomical position. Once the conforming anatomical position corresponds with the predetermined anatomical position, a second K-wire inserts through the second aperture of the selected drill guide and into the second bone such that the first and second K-wires and the drill guide retain the first bone and the second bone in a retained anatomical position that corresponds with the predetermined anatomical position. An implant including a second distance between its first and second legs that corresponds with the preset distance between the first and second apertures of the selected drill guide is selected. The cannulated drill bit via its cannulation inserts over the first K-wire such that the cannulated drill bit contacts the first bone. The cannulated drill bit then is used to drill over the first K-wire and into the first bone until the cannulated drill bit creates a first drilled hole. The cannulated drill bit is removed from over the first K-wire and inserted over the second K-wire such that the cannulated drill bit contacts the second bone. The cannulated drill bit then is used to drill over the second K-wire and into the second bone until the cannulated drill bit creates a second drilled hole. After removal of the cannulated drill bit from over the second K-wire, the drill guide is removed from over the first and second K-wires, the first K-wire is removed from the first drilled hole, and the second K-wire is removed from the second drilled hole. The implant insertion device then inserts the first leg of the implant into the first drilled hole and the second leg of the implant into the second drilled hole. Once inserted, the implant attempts to transition from its constrained insertion shape to its unconstrained shape such that the implant continuously compresses the first bone and the second bone thereby holding the first bone and the second bone in the predetermined anatomical position.

The orthopedic fixation system alternatively is used as follows to fuse bone, bones, or bone pieces, and, by way of example, a first bone and a second bone. Once the first bone and the second bone are manipulated into a conforming anatomical position that corresponds with a predetermined anatomical position, the fixed distances of the sizing guide are sequentially positioned across a fusion site of the first bone and the second bone until a fixed distance indicates a desired distance across the first bone and the second bone for implantation of an implant into the first bone and the second bone. An implant with a second distance between its first and second legs corresponding with the fixed distance of the sizing guide indicating the desired distance is selected along with a drill guide with a preset distance between its first aperture and its second aperture corresponding with the second distance between the first and second legs of the selected implant. The selected drill guide is placed atop the first bone and the second bone such that the drill guide spans a fusion site of the first bone and the second bone, whereby the first aperture of the drill guide is located at the first bone and the second aperture of the drill guide is located across the fusion site at the second bone. A first K-wire is inserted through the first aperture of the drill guide and into the first bone and a second K-wire is inserted through the second aperture of the drill guide and into the second bone such that the selected drill guide and the first and second K-wires retain the first bone and the second bone in a retained anatomical position. With the first and second bones held in the retained anatomical position, a verification of whether the retained anatomical position corresponds with the predetermined anatomical position is performed. When the retained anatomical position does not correspond with the predetermined anatomical position, the first K-wire is removed from the first aperture of the selected drill guide, the second K-wire is removed from the second aperture of the selected drill guide, and the selected drill guide is removed from atop the first bone and the second bone. After manipulating the first bone and the second bone again into a conforming anatomical position that corresponds with the predetermined anatomical position, the selected drill guide and the first and second K-wires as previously described hold the first bone and the second bone in a retained anatomical position while a verification of whether the retained anatomical position corresponds with the predetermined anatomical position is performed. The first bone and the second bone are repeatedly manipulated into a conforming anatomical position and retained using the selected drill guide and the first and second K-wires until the retained anatomical position and thus the conforming anatomical position corresponds with the predetermined anatomical position. Once the retained anatomical position corresponds with the predetermined anatomical position, the cannulated drill bit via its cannulation inserts over the first K-wire such that the cannulated drill bit contacts the first bone. The cannulated drill bit then is used to drill over the first K-wire and into the first bone until the cannulated drill bit creates a first drilled hole. The cannulated drill bit is removed from over the first K-wire and inserted over the second K-wire such that the cannulated drill bit contacts the second bone. The cannulated drill bit then is used to drill over the second K-wire and into the second bone until the cannulated drill bit creates a second drilled hole. After removal of the cannulated drill bit from over the second K-wire, the drill guide is removed from over the first and second K-wires, the first K-wire is removed from the first drilled hole, and the second K-wire is removed from the second drilled hole. The implant insertion device then inserts the first leg of the implant into the first drilled hole and the second leg of the implant into the second drilled hole. Once inserted, the implant attempts to transition from its constrained insertion shape to its unconstrained shape such that the implant continuously compresses the first bone and the second bone thereby holding the first bone and the second bone in the predetermined anatomical position.

When using the orthopedic fixation system, a first K-wire guide may be inserted into the first aperture of the selected drill guide prior to the first K-wire in order to stabilize the first K-wire within the first aperture of the selected drill guide. The first K-wire guide is removed from the selected drill guide and from over the first K-wire prior to inserting the cannulated drill bit over the first K-wire. Likewise, the first K-wire guide is removed from the selected drill guide and from over the first K-wire prior to removing the first K-wire from the first bone. A second K-wire guide may be inserted into the second aperture of the selected drill guide prior to the second K-wire in order to stabilize the second K-wire within the second aperture of the selected drill guide. The second K-wire guide is removed from the selected drill guide and from over the second K-wire prior to inserting the cannulated drill bit over the second K-wire. Likewise, the second K-wire guide is removed from the selected drill guide and from over the second K-wire prior to removing the second K-wire from the second bone.

After drilling a first drilled hole in the first bone, the first K-wire may be removed from the first drilled hole and the first aperture of the selected drill guide such that a first locating pin may be inserted through the first aperture and into the first drilled hole. Likewise, after drilling a second drilled hole in the second bone, the second K-wire may be removed from the second drilled hole and the second aperture of the selected drill guide such that a second locating pin may be inserted through the second aperture and into the second drilled hole. Upon the removal of the selected drill guide from over the first and second locating pins, the first and second locating pins located the first and second drilled holes, respectively. The first locating pin is removed from the first drilled hole and the second locating pin is removed from the second drilled hole prior to the insertion of the selected implant.

Prior to the insertion of the selected implant, the depths of the first and second drilled holes are determined in order to permit selection of an implant with first and second legs having a length corresponding with the depth of the first and second drilled holes. Moreover, after the insertion of the selected implant, the implant is tamped to an implanted position whereby the first leg resides within the first drilled hole, the second leg resides in the second drilled hole, and the bridge abuts the first bone and the second bone across the fusion site thereof.

It is therefore an object of the present invention to provide an orthopedic fixation system that holds bone, bones, or bone pieces in an anatomical alignment such that a determination of whether the held anatomical alignment corresponds with a desired anatomical alignment may be performed.

It is another object of the present invention to provide an orthopedic fixation system that holds bone, bones, or bone pieces in an anatomical alignment corresponding with a desired anatomical alignment during the drilling of holes into the bone, bones, or bone pieces which are then utilized in the insertion of an implant into the bone, bones, or bone pieces.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

DETAILED DESCRIPTION OF THE PREFERRED EMBODIMENTS

Figure 1:
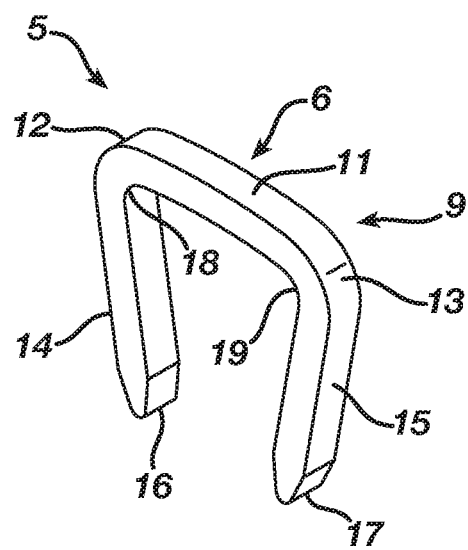
FIG. 1 is an isometric view illustrating an implant of an orthopedic fixation system according to the present invention in an unconstrained shape.

As required, detailed embodiments of the present invention are disclosed herein; however, it is to be understood that the disclosed embodiments are merely exemplary of the invention, which may be embodied in various forms. It is further to be understood that the figures are not necessarily to scale, and some features may be exaggerated to show details of particular components or steps.

FIGS. 1-13 illustrate an orthopedic fixation system 5 according to a preferred embodiment of the present invention. Referring to FIGS. 1-4, the orthopedic fixation system 5 includes an implant 6 and a mechanical constraint, such as the implant insertion device 7, both of which are typically enclosed in a packaging. While the orthopedic fixation system 5 illustrated in FIGS. 1-4 show a single implant 6 and implant insertion device 7, one of ordinary skill in the art will recognize that the orthopedic fixation system 5 may include multiple implants 6 and implant insertion devices 7 packaged either separately or in combination.

Figure 2:
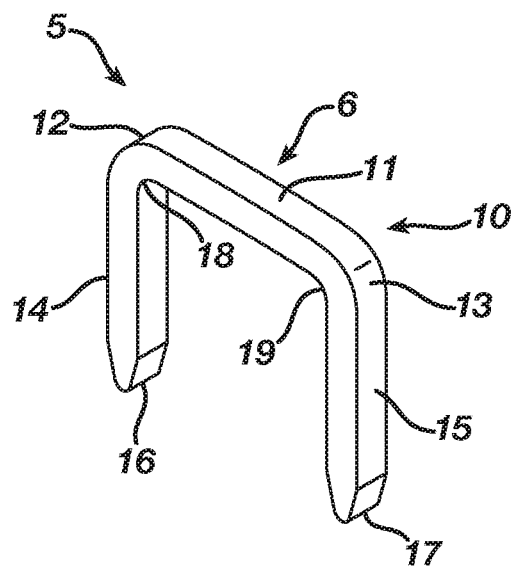
FIG. 2 is an isometric view illustrating the implant in a constrained insertion shape.

FIG. 1 illustrates the implant 6 in an unconstrained shape 9, whereas FIG. 2 illustrates the implant 6 in a constrained insertion shape 10. The implant 6 in the preferred embodiment accordingly is a continuous compression implant that assists in fusing bone, bones, or bone pieces. The implant 6 may be manufactured from any elastic material suitable for orthopedic use, such as a shape memory material (e.g., Nitinol). In the preferred embodiment, the implant 5 includes a bridge 11 having a first end 12 and a second end 13 and further a first leg 14 extending from the first end 12 of the bridge 11 and a second leg 15 extending from the second end 12 of the bridge 11. The first and second legs 14 and 15, which have a respective tip 16 and 17, may include barbs thereon that improve the pull-out resistance of the implant 6. Although the preferred embodiment discloses the implant 6 as including the first and second legs 14 and 15, one of ordinary skill in the art will recognize that the implant 6 may include three or more legs.

The bridge 11 in the preferred embodiment includes a transition section 18 disposed at the first end 12 and a transition section 19 at the second end 13. The natural shape of the implant 6, as illustrated in FIG. 1, is its unconstrained shape 9 where the transition sections 18 and 19, respectively, locate the first and second legs 14 and 15 in an unconstrained position, which, in the preferred embodiment, is convergent whereby the first and second legs 14 and 15 are spaced apart at a first distance. Nevertheless, as illustrated in FIG. 2, the implant 6 is deformable under the action of superelasticity or shape memory to the constrained insertion shape 10 where the transition sections 18 and 19, respectively, deform to store energy while also moving the first and second legs 14 and 15 to a constrained insertion position, which, in the preferred embodiment, is substantially parallel whereby the first and second legs 14 and 15 are spaced apart at a second distance that is greater than the first distance. While the orthopedic fixation system 5 in the preferred embodiment discloses a single implant 6, one of ordinary skill in the art will recognize that the orthopedic fixation system 5 may include multiple implants 6 whereby the implants 6 each include bridges 11 with different lengths such that their first and second legs 14 and 15 are spaced apart at different distances. Moreover, one of ordinary skill in the art will recognize that the orthopedic fixation system 5 may include multiple implants 6 whereby the implants 6 each include first and second legs 14 and 15 with lengths different from the first and second legs 14 and 15 of the other implants 6.

Since the constrained insertion shape 10 is not the natural shape of the implant 6, the orthopedic fixation system 5 includes the mechanical constraint, such as the implant insertion device 7, that mechanically constrains the implant 6. Release of the mechanical constraint after implantation of the implant 6 into bone, bones, or bone pieces results in the implant 6 attempting to transition from its constrained insertion shape 10 to its unconstrained shape 9 and the first and second legs 14 and 15 attempting to move from their constrained insertion position to their unconstrained position such that the implant 6 delivers the energy stored in the transition sections 18 and 19, thereby exerting a compressive force to the bone, bones, or bone pieces.

Figure 3:
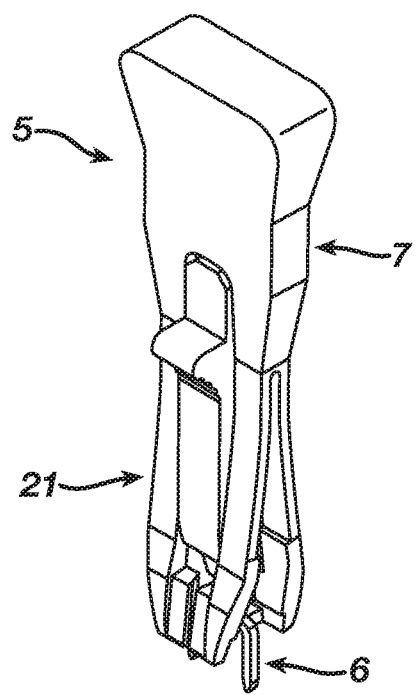
FIG. 3 is an isometric view illustrating an implant insertion device of the orthopedic fixation system according to the present invention in an implant disengagement position prior to the loading of the implant insertion device with the implant.
Figure 4:
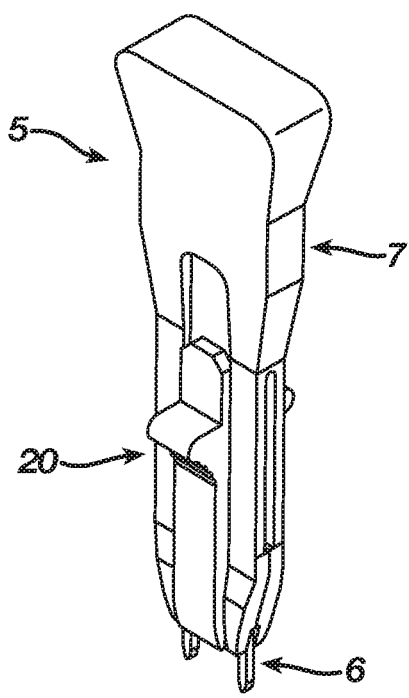
FIG. 4 is an isometric view illustrating the implant insertion device in an implant engagement position whereby the implant insertion device is loaded with the implant.
Figure 5:
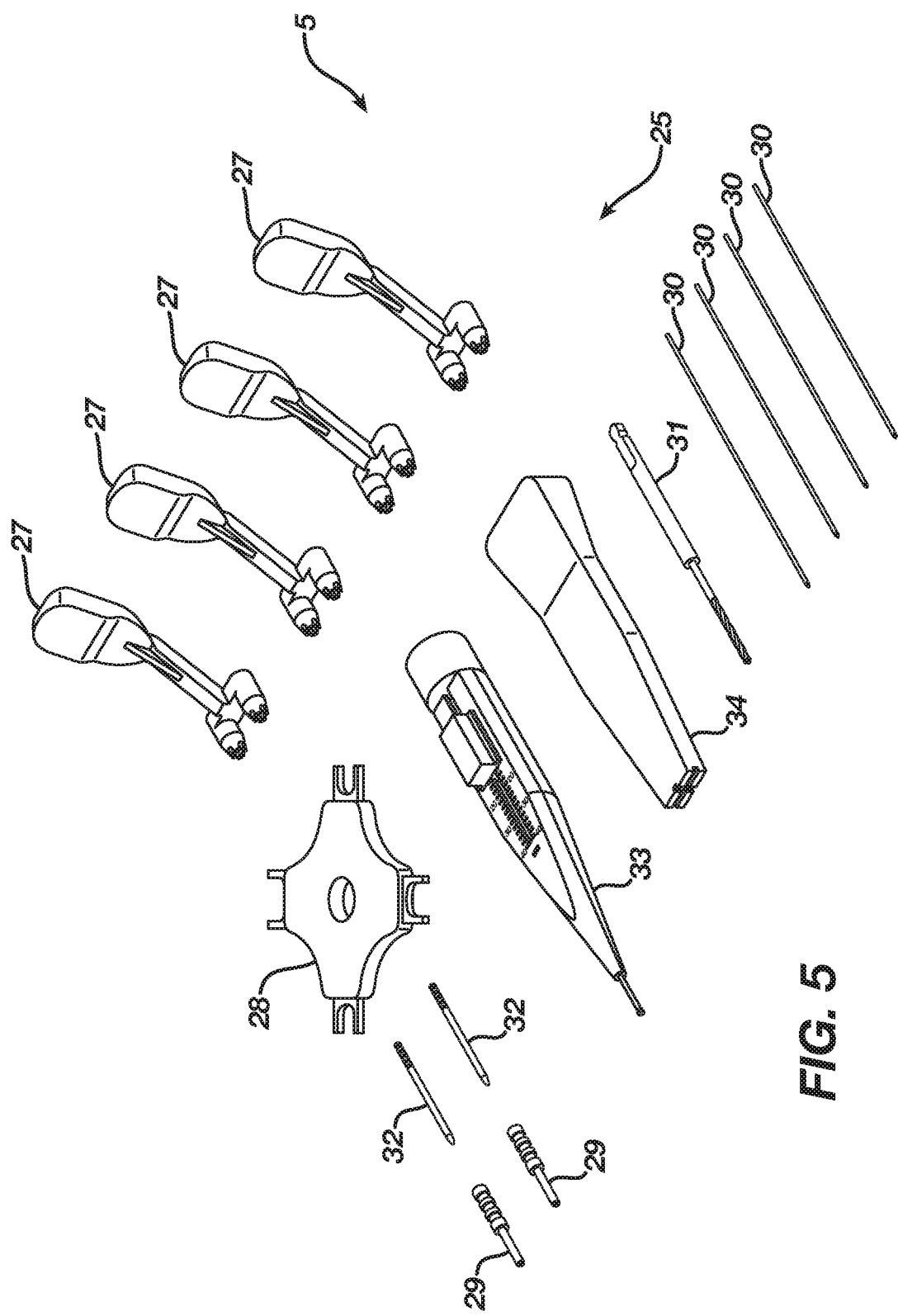
FIG. 5 is an isometric view illustrating instruments of the orthopedic fixation system according to the present invention.

FIGS. 3 and 4 illustrate the implant insertion device 7, which is presented herein as an example of a mechanical constraint suitable to engage the implant 6 and maintain the implant 6 in its constrained insertion shape 10. FIG. 3 illustrates the implant insertion device 7 prior to its loading with the implant 6, whereas FIG. 4 illustrates the implant insertion device 7 loaded with the implant 6. Implant insertion devices suitable to maintain the implant 6 in its constrained insertion shape 10, such as the exemplary implant insertion device 7 which is disclosed in US Patent Publication No. US 20160074037 A1, are available from DePuy Synthes Products, Inc., 325 Paramount Drive, Raynham, Mass. 02767.

The implant insertion device 7 resides in either an implant disengagement position 20 as illustrated in FIG. 3 or an implant engagement position 21 as illustrated in FIG. 4 and is movable therebetween. In the implant disengagement position 20, the implant insertion device 7 releases the implant 6 with no obstruction. In the implant engagement position 21, the implant insertion device 7 engages the implant 6 and maintains the implant 6 in its constrained insertion shape 10. In addition, the implant insertion device 7 allows a surgeon to manipulate the implant 6 and insert the implant 6 into bone, bones, or bone pieces that require fixating. The implant insertion device 7 in the preferred embodiment is packaged loaded with the implant 6; nevertheless, one of ordinary skill in the art will recognize that the implant insertion device 7 may be packaged with the implant 6 unloaded.

While the orthopedic fixation system 5 in the preferred embodiment discloses a single implant insertion device 7 loaded with the implant 6, one of ordinary skill in the art will recognize that the orthopedic fixation system 5 may include multiple implant insertion devices 7 each loaded with a different sized implant 6 that are packaged either separately or in combination. Moreover, although the preferred embodiment discloses an implant insertion device 7 engaging an implant 6 with first and second legs 14 and 15, one of ordinary skill in the art will recognize that an implant insertion device 7 capable of engaging an implant 6 with three or more legs may be provided.

Referring to FIGS. 5-13, the orthopedic fixation system 5 includes instruments 25, which typically are enclosed in a packaging. The instruments 25 in the preferred embodiment include one or more drill guides 27, one or more K-wires 30, a cannulated drill bit 31, and optionally a sizing guide 28, one or more K-wire guides 29, one or more locating pins 32, a depth gauge 33, and a tamp 34. The orthopedic fixation system 5 includes one or more drill guides 27 that in the preferred embodiment are sized differently in order to accommodate use of different sized implants 6. Nevertheless, one of ordinary skill in the art will recognize that the orthopedic fixation system 5 may include only a single drill guide 27.

Figure 6:
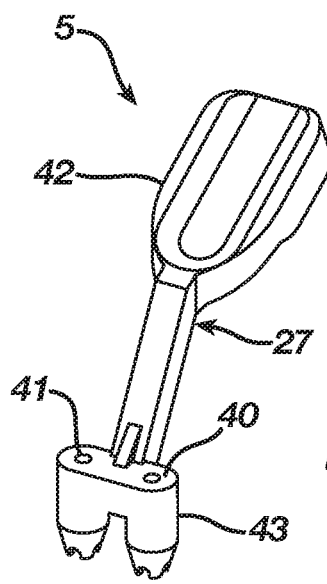
FIG. 6 is an isometric view illustrating a drill guide of the instruments.

FIG. 6 illustrates a drill guide 27 which is an example of the one or more drill guides 27 of the orthopedic fixation system 5. The drill guide 27 as illustrated in FIG. 6 includes a first aperture 40 and a second aperture 41 therethrough. The first aperture 40 and the second aperture 41 are spaced apart a distance that corresponds with and in the preferred embodiment is substantially equal to the second distance between the first and second legs 14 and 15 of the implant 6, which is the distance between the first and second legs 14 and 15 when the first and second legs 14 and 15 reside in their constrained insertion position. The drill guide 27 accordingly permits the drilling of holes into bone, bones, or bone pieces that are spaced apart a distance that receives therein the implant 6 when the implant 6 resides in its constrained insertion shape 10 and correspondingly when the first and second legs 14 and 15 reside in their constrained insertion position. The drill guide 27 in the preferred embodiment includes a handle 42 and a body 43 including the first and second apertures 40 and 41 therethrough.

While the drill guide 27 illustrated in FIG. 6 includes first and second apertures 40 and 41 spaced apart a distance corresponding with the distance between the first and second legs 14 and 15 of the implant 6 when the first and second legs 14 and 15 reside in their constrained insertion position, one of ordinary skill in the art will recognize that additional drill guides 27 of the orthopedic fixation system 5 will include first and second apertures 40 and 41 spaced apart at distances that correspond with the constrained insertion positions of first and second legs 14 and 15 for different sized implants 6 when the different sized implants 6 reside in their constrained insertion shape 10. Moreover, although the preferred embodiment discloses a drill guide 27 with first and second apertures 40 and 41 therethrough, one of ordinary skill in the art will recognize that a drill guide 27 that permits the drilling of three or more holes may be provided.

Figure 7:
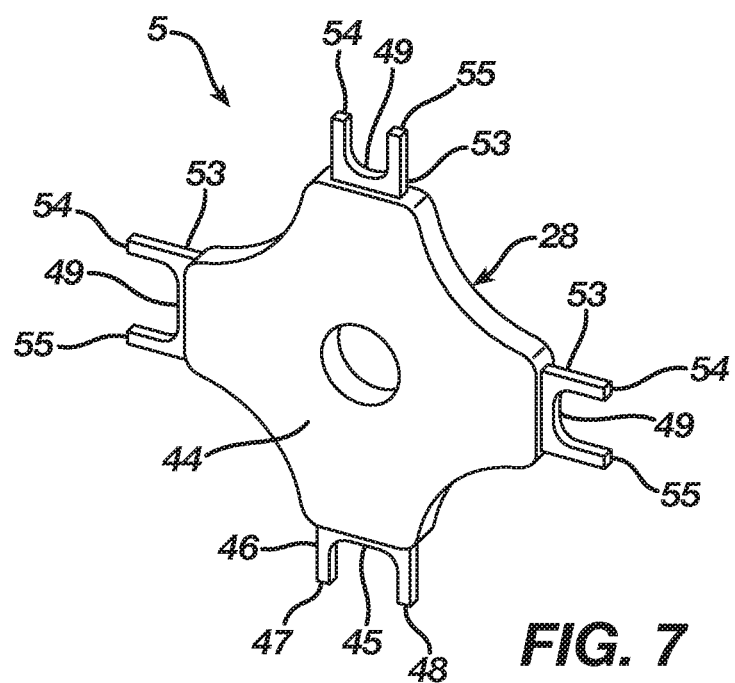
FIG. 7 is an isometric view illustrating a sizing guide of the instruments.

The sizing guide 28 as illustrated in FIG. 7 facilitates a measurement across bone, bones, or bone pieces requiring fusion in order to permit selection of an implant 6 with a bridge 11 having a length corresponding to a fusion site across the bone, bones, or bone pieces. The sizing guide 28 includes a body 44 that defines at a perimeter thereof at least one fixed distance 45. In particular, a protrusion 46 extends from the body 44 in order to delineate the fixed distance 45. The protrusion 46 in the preferred embodiment includes first and second discrete projections 47 and 48 that aid in a visual verification of the fixed distance 45. The fixed distance 45 as delineated by the protrusion 46 and thus the first and second discrete projections 46 and 47 corresponds with and in the preferred embodiment is substantially equal to the distance between the first aperture 40 and the second aperture 41 of the drill guide 27. As such, the fixed distance 45 corresponds with and in the preferred embodiment is substantially equal to the second distance between the first and second legs 14 and 15 of the implant 6, which is the distance between the first and second legs 14 and 15 when the first and second legs 14 and 15 reside in their constrained insertion position. The sizing guide 28 when located next to bone, bones, or bone pieces with the protrusion 46 and thus the first and second discrete projections 46 and 47 positioned adjacent the bone, bones, or bone pieces permits a measurement across a fusion site of the bone, bones, or bone pieces that determines if the implant 6 illustrated in the preferred embodiment is the desired size for implantation. While the sizing guide 28 has been described with reference to the fixed distance 45, one of ordinary skill in the art will recognize that the body 44 of the sizing guide 28 defines along its perimeter multiple additional fixed distances 49 delineated by multiple protrusions 53 including multiple first and second discrete projections 54 and 55 that correspond with and in the preferred embodiment are substantially equal to the distance between the first and second apertures 40 and 41 of different sized drill guides 27. The sizing guide 28 accordingly through the use of the fixed distance 45 and the multiple additional fixed distances 49 permits a measurement across a fusion site of bone, bones, or bone pieces that determines which different sized implant 6 of the orthopedic fixation system 5 has a desired length (i.e., first and second leg 14 and 15 distance) for implantation.

Figure 8:
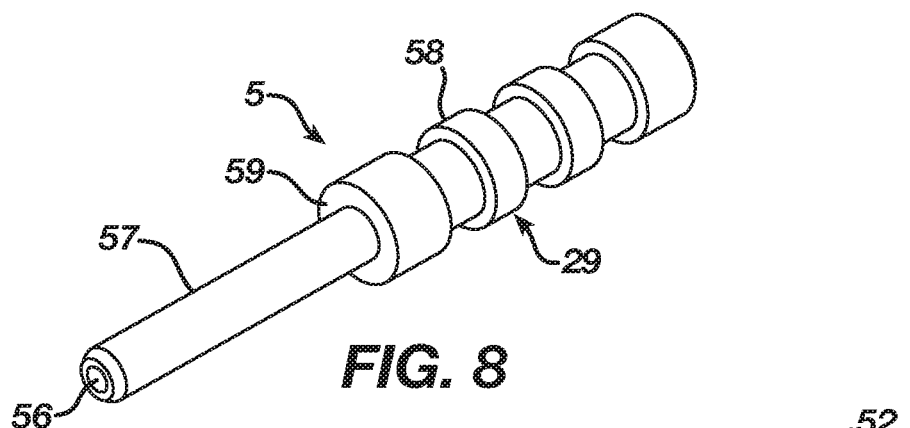
FIG. 8 is an isometric view illustrating a K-wire guide of the instruments.

FIG. 8 illustrates a K-wire guide 29 which is an example of the one or more K-wire guides 29 of the orthopedic fixation system 5. The K-wire guide 29 includes a cannulation 56 therethrough that is sized to receive a K-wire 30 therethrough. The K-wire guide 29 includes a tube 57 defining the cannulation 56 and a grip 58 defining a stop 59 extending from the tube 57. The tube 57 is sized to fit within either the first and second apertures 40 and 41 of the drill guide 27. The grip 58 permits grasping of the K-wire guide 29, while the stop 58 is sized to engage a top of the drill guide 27 at either the first and second apertures 40 and 41 in order to arrest the insertion of the tube 57 within the drill guide 27 such that the tube 57 does not extend from a bottom of the drill guide 27. A K-wire guide 29 once inserted into the drill guide 27 aids in retaining and stabilizing a K-wire 30 within the drill guide 27 and thus also within a bone, bones, or bone pieces into which the K-wire 30 is implanted. While a K-wire guide 29 enhances the stability of a K-wire 30 within the drill guide 27 and thus also within a bone, bones, or bone pieces, one of ordinary skill in the art will recognize that the drill guide 27 and a K-wire 30 may be utilized without the benefit of a K-wire guide 29. One of ordinary skill in the art will understand that the number of K-wire guides 29 employed corresponds with the number of apertures in the drill guide 27 and thus the number of legs for the implant 6.

Figure 9:
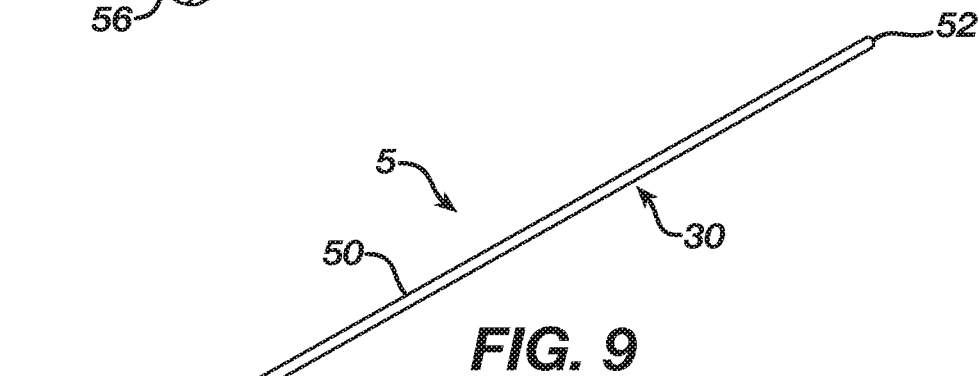
FIG. 9 is an isometric view illustrating a K-wire of the instruments.

FIG. 9 illustrates a K-wire 30 which is an example of the one or more K-wires 30 of the orthopedic fixation system 5. The K-wire 30, which is sized to fit within the K-wire guide 29 and thus also the first and second apertures 40 and 41 of the drill guide 27, is a cylindrical rod 50 having a first pointed insertion end 51 and a second end 52. The K-wires 30 of the orthopedic fixation system 5 in the preferred embodiment are the same length and diameter; nevertheless, one or ordinary skill in the art will recognize that the K-wires 30 may have different lengths and diameters as necessary. Once a bone, bones, or bone pieces requiring fusion are aligned, a drill guide 27 is located adjacent therewith, and first and second K-wire guides 29 are inserted respectively into the first and second apertures 40 and 41 of the drill guide 27, a first K-wire 30 inserts via its first pointed insertion end 51 through the cannulation 56 of the first K-wire guide 29 and into the bone, bones, or bone pieces. Likewise, a second K-wire 30 inserts via its first pointed insertion end 51 through the cannulation 56 of the second K-wire guide 29 and into the bone, bones, or bone pieces. The K-wires 30 accordingly in combination with the K-wire guides 29 and the drill guide 27 hold the bone, bones, or bone pieces such that their alignment may be verified prior to the drilling of holes therein. While use of K-wire guides 29 in combination with the drill guide 27 and K-wires 30 enhances the ability of the drill guide 27 and the K-wires 30 to hold the bone, bones, or bone pieces in alignment, one of ordinary skill in the art will recognize that the drill guide 27 and the K-wires 30 may be utilized without the benefit of the K-wire guides 29. Furthermore, the K-wires 30 in combination with the drill guide 27 facilitate the drilling of holes in the bone, bones, or bone pieces while the K-wires 30 and the drill guide 27 retain the bone, bones, or bone pieces in alignment. Although the foregoing illustrates first and second K-wires 30, one of ordinary skill in the art will understand that the number of K-wires 30 employed corresponds with the number of apertures in the drill guide 27 and thus the number of legs for the implant 6.

Figure 10:
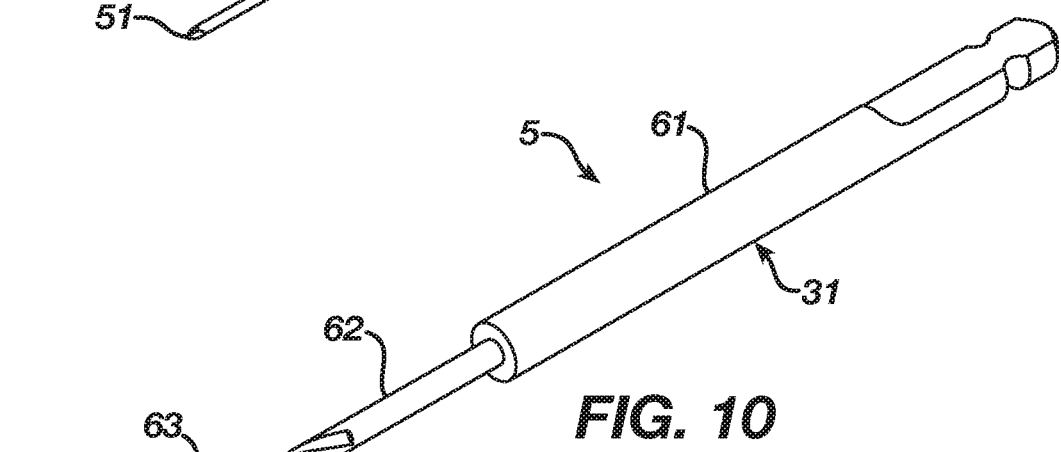
FIG. 10 is an isometric view illustrating a cannulated drill bit of the instruments.

The cannulated drill bit 31 as illustrated in FIG. 10 includes a cannulation 60 therethrough that permits the cannulated drill bit 31 to fit over the K-wire 30. The cannulated drill bit 31 includes a shank 61 and a body 62 having flutes 63 along its length and terminating in a cutting edge 64. The body 62 and its cutting edge 64 have a diameter that creates a drilled hole in bone, bones, or bone pieces appropriately sized to receive one of the first and second legs 14 and 15 of the implant 6 therein. Once a bone, bones, or bone pieces requiring fusion are aligned and retained by K-wires 30 and the drill guide 27, the cannulated drill bit 31 via its cannulation 60 inserts over a first K-wire 30 whereby the cannulated drill bit 31 drills a first drilled hole in the bone, bones, or bone pieces. Likewise, the cannulated drill bit 31 via its cannulation 60 inserts over a second K-wire whereby the cannulated drill bit 31 drills a second drilled hole in the bone, bones, or bone pieces. The cannulated drill bit 31 accordingly due to its cannulation 60 facilitates the creation of drilled holes in bone, bones, or bone pieces while the K-wires 30 in combination with the drill guide 27 retain the bone, bones, or bone pieces in alignment. While the cannulated drill bit 31 has been described for use with the implant 6 illustrated in the preferred embodiment, one of ordinary skill in the art will recognize that the orthopedic fixation system 5 may include multiple cannulated drill bit 31 that correspond in length and diameter for use with different sized implants 6. Moreover, although the foregoing illustrates first and second drilled holes, one of ordinary skill in the art will understand that the number of drilled holes corresponds with the number of apertures in the drill guide 27 and thus the number of legs for the implant 6.

Figure 11:
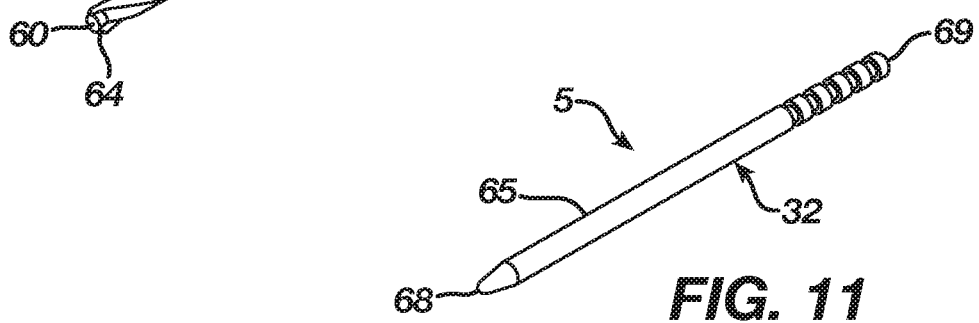
FIG. 11 is an isometric view illustrating a locating pin of the instruments.

FIG. 11 illustrates a locating pin 32 which is an example of the one or more locating pins 32 of the orthopedic fixation system 5. The locating pin 32, which is sized to fit within the first and second apertures 40 and 41 of the drill guide 27, is a cylindrical rod 65 having a first pointed insertion end 68 and a second end 69. The locating pins 32 of the orthopedic fixation system 5 in the preferred embodiment are the same length and diameter; nevertheless, one or ordinary skill in the art will recognize that the locating pins 32 may have different lengths and diameters as necessary. Once a first drilled hole is formed in bone, bones, or bone pieces followed by the removal of the cannulated drill bit 31 and a first K-wire 30 from the first aperture 40 of the drill guide 27, a first locating pin 32 inserts via its first pointed insertion end 68 through the first aperture 40 of the drill guide 27 and into the first drilled hole created in the bone, bones, or bone pieces. Likewise, after a second drilled hole is formed in the bone, bones, or bone pieces followed by the removal of the cannulated drill bit 31 and a second K-wire 30 from the second aperture 41 of the drill guide 27, a second locating pin 32 inserts via its first pointed insertion end 68 through the second aperture 41 of the drill guide 27 and into the second drilled hole created in the bone, bones, or bone pieces. Upon the removal of the drill guide 27 from over the first and second locating pins 32, the first and second locating pins 32 mark the locations of the first and second drilled holes. Although the foregoing illustrates first and second locating pins 32, one of ordinary skill in the art will understand that the number of locating pins 32 employed corresponds with the number of apertures in the drill guide 27 and thus the number of legs for the implant 6.

Figure 12:
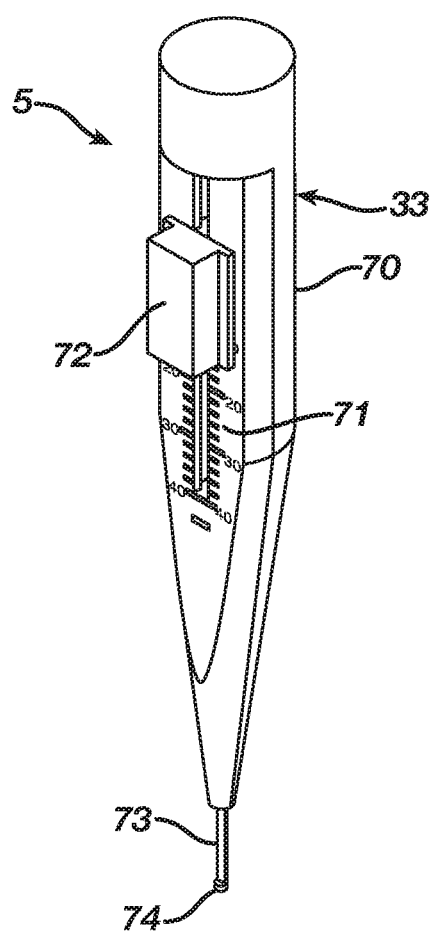
FIG. 12 is an isometric view illustrating a depth gauge of the instruments.

The depth gauge 33 as illustrated in FIG. 12 facilitates a determination of drilled hole depth into bone, bones, or bone pieces in order to permit selection of an implant 6 with first and second legs 14 and 15 having a length corresponding to the depth of the drilled hole. The depth gauge 33 includes a body 70 marked thereon with a scale 71 indicative of drilled hole depth. In the preferred embodiment, the scale 71 is delineated in millimeters although one of ordinary skill in the art will recognize that other units of measure may be used. The depth gauge 33 includes a slider 72 located exterior to the body 70 and a rod 73 located interior to the body 70 and coupled with the slider 72. The rod 73 terminates in a hook 74 that permits engagement of the rod 73 with bone, bones, or bone pieces having a drilled hole therein. The slider 72 moves along the body 70 relative to the scale 71 such that the slider 72 facilitates extension of the rod 73 from the body 70 and the retraction of the rod into the body 70. The slider 72 and the rod 73 are configured such that the location of the slider 72 along the scale 71 furnishes a measurement that corresponds with the extension of the rod 73 from the body 70. As such, the extension of the rod 73 from the body 70 using the slider 72 into a drilled hole formed in bone, bones, or bone pieces reflects drilled hole depth, thereby allowing measurement thereof.

Figure 13:
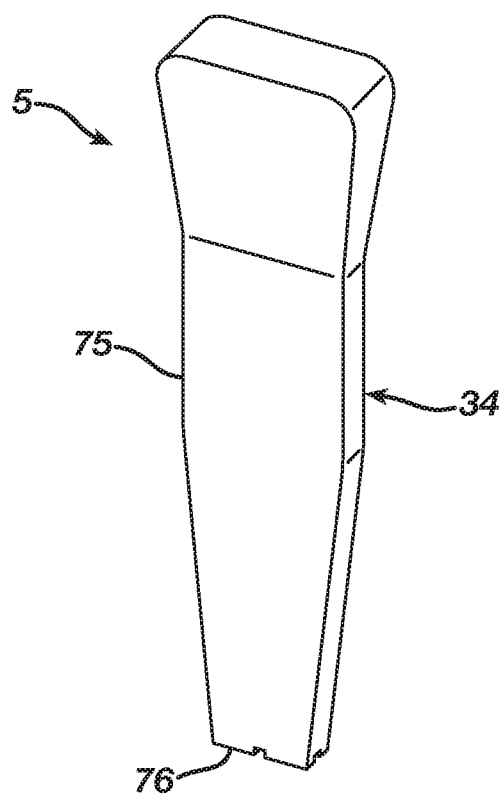
FIG. 13 is an isometric view illustrating a tamp of the instruments.

The tamp 34 as illustrated in FIG. 13 facilitates tamping of an implant 6 to its implanted position whereby the first and second legs 14 and 15 reside within bone, bones, or bone pieces and the bridge 11 abuts the bone, bones, or bone pieces. The tamp 34 includes a body 75 terminating in an implant engagement end 76. In the preferred embodiment, the implant engagement end 76 includes protrusions defining grooves that receives therein a bridge 11 of an implant 6. The tamp 34, accordingly, once engaged with a bridge 11 of an implant 6, permits pushing of the implant 6 to its implanted position.

In the preferred embodiment, the implant 6 loaded on the implant insertion device 7 is packaged separately from the instruments 25 in order to allow the selection and then opening of only a single implant 6 and implant insertion device 7. Nevertheless, one of ordinary skill in the art will recognize that an implant 6 loaded on an implant insertion device 7 or multiple implants 6 each loaded on an implant insertion device 7 may be packaged in combination with the instruments 25. Moreover, one of ordinary skill in the art will recognize that implants 6 loaded on implant insertion devices 7 as well as the instruments 25 may be packaged separately.

Figure 14:
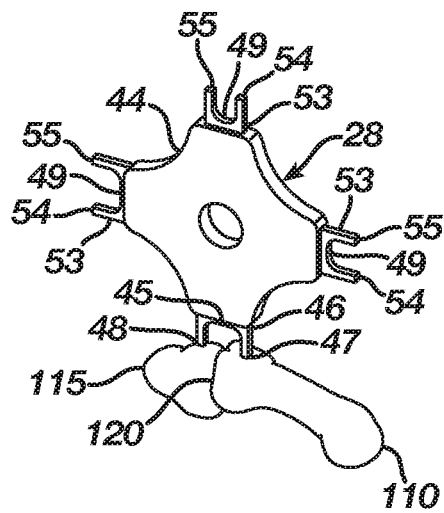
FIGS. 14-25 are isometric views illustrating use of the orthopedic fixation system in implanting an implant thereof into bone, bones, or bone pieces.

FIGS. 14-25 illustrate a method whereby a surgeon employs the orthopedic fixation system 5 of the present invention to implant an implant 6 thereof into bone, bones, or bone pieces, and, in particular, into a first bone 110 and a second bone 115 which is presented herein as an example. The surgeon determines a predetermined anatomical position of the first bone 110 and the second bone 115, which, in the preferred embodiment, is an anatomical position of the first bone 110 and the second bone 115 that is desirable to promote a fusion and thus a healing thereof. Referring to FIG. 14, the surgeon places the first bone 110 and the second bone 115 in a conforming anatomical position, which, in the preferred embodiment, is an anatomical position of the first bone 110 and the second bone 115 that corresponds with the predetermined anatomical position. After locating the first bone 110 and the second bone 115 in their conforming anatomical position, the surgeon employs the sizing guide 28 to measure across a fusion site 120 of the first bone 110 and the second bone 115 in order to determine which implant 6 of the orthopedic fixation system 5 has a desired length (i.e., first and second leg 14 and 15 distance in their constrained insertion position) for implantation into the first bone 110 and the second bone 115 across the fusion site 120 thereof. In particular, the surgeon sequentially positions the first and second discrete projections 46 and 47 of the protrusion 46 and the multiple first and second discrete projections 54 and 55 of the multiple protrusions 53 across the fusion site 120 for the first bone 110 and the second bone 115 until a correct size for an implant 6 is established.

Figure 15:
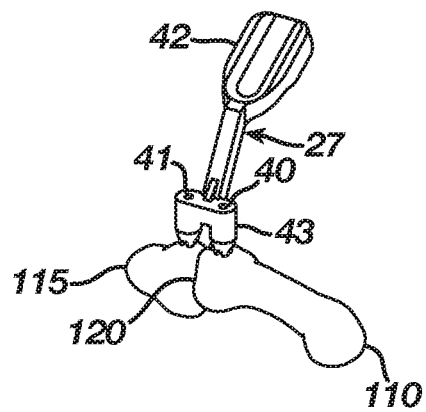

Referring to FIG. 15, the surgeon, after selecting an implant 6, chooses a drill guide 27 of the orthopedic fixation system 5 with a first aperture 40 and a second aperture 41 spaced apart a distance that corresponds with the distance between the first and second legs 14 and 15 of the selected implant 6 when the selected implant 6 resides in its constrained insertion shape 10 and the first and second legs 14 and 15 are located in their constrained insertion position. With the first bone 110 and the second bone 115 located in their conforming anatomical position, the surgeon places the drill guide 27 atop the first bone 110 and the second bone 115 with the drill guide 27 located across the fusion site 120 whereby the first aperture 40 resides on a first side of the fusion site 120 and the second aperture 41 resides on a second side of the fusion site 120. The surgeon may contour the fusion site 120 of the first bone 110 and the second bone 115 to ensure proper contact of the drill guide 27 with the first bone 110 and the second bone 115. The drill guide 27 accordingly permits a drilling of first and second drilled holes in the first bone 110 and the second bone 115 such that the first and second drilled holes are positioned at a desired location and spacing across the fusion site 120 of the first bone 110 and the second bone 115 for an insertion into the first bone 110 and the second bone 115 across their fusion site 120 of the first and second legs 14 and 15 of the selected implant 6 when the selected implant 6 resides in its constrained insertion shape 10 and the first and second legs 14 and 15 are located in their constrained insertion position.

Figure 16:
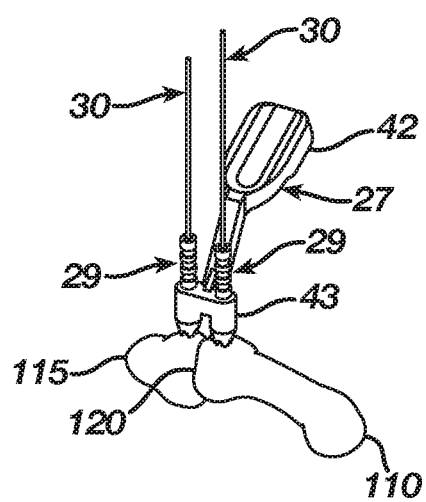

Referring to FIG. 16, with the first bone 110 and the second bone 115 located in their conforming anatomical position and the drill guide 27 placed atop the first bone 110 and the second bone 115, the surgeon inserts a first K-wire guide 29 into the first aperture 40 of the drill guide 27 and a second K-wire guide 29 into the second aperture 41 of the drill guide 27. The surgeon then inserts a first K-wire 30 through the cannulation 56 of the first K-wire guide 29 and into the first bone 110. Likewise, the surgeon inserts a second K-wire 30 through the cannulation 56 of the second K-wire guide 29 and into the second bone 115. Once inserted into the first bone 110 and the second bone 115, the first and second K-wires 30 in combination with the first and second K-wire guides 29 and the drill guide 27 retain the first bone 110 and the second bone 115 in a retained anatomical position, which, in the preferred embodiment, is where the first and second K-wires 30, the first and second K-wire guides 29, and the drill guide 27 hold the first bone 110 and the second bone 115 in their conforming anatomical position.

An advantage of the orthopedic fixation system 5 according to the present invention includes holding the first bone 110 and the second bone 115 in their retained anatomical position thereby providing the surgeon with an ability to verify whether the retained anatomical position and thus the conforming anatomical position correspond with the predetermined anatomical position prior to an actual drilling of drilled holes. In particular, once the first and second K-wires 30, the first and second K-wire guides 29, and the drill guide 27 retain the first bone 110 and the second bone 115 in their retained anatomical position, the surgeon verifies whether the retained anatomical position conforms with the predetermined anatomical position using a visual inspection, a measuring tool, fluoroscopy, or the like. If the surgeon determines that the retained anatomical position conforms with the predetermined anatomical position, then the surgeon may proceed with the drilling of drilled holes. Alternatively, if the surgeon determines that the retained anatomical position does not conform with the predetermined anatomical position, then the surgeon may remove the first and second K-wires 30 from the first bone 110 and the second bone 115 and the first and second K-wire guides 29 as well as the first and second K-wire guides 29 from the drill guide 27 and the drill guide 27 from the first bone 110 and the second bone 115. This permits the surgeon to again attempt placement of the first bone 110 and the second bone 115 in a conforming anatomical position followed by the use of the drill guide 27, the first and second K-wire guides 29, and the first and second K-wires 30 to hold the first bone 110 and the second bone 115 in a retained anatomical position as previously described. After a placement and holding of the first bone 110 and the second bone 115 results in the first bone 110 and the second bone 115 being retained in a retained anatomical position that conforms with the predetermined anatomical position, the surgeon then may proceed with the drilling of drilled holes. While use of K-wire guides 29 in combination with the drill guide 27 and K-wires 30 enhances the ability of the drill guide 27 and the K-wires 30 to hold the first bone 110 and the second bone 115 in a retained anatomical position, one of ordinary skill in the art will recognize that the drill guide 27 and the K-wires 30 may be utilized without the benefit of the K-wire guides 29.

Figure 24:
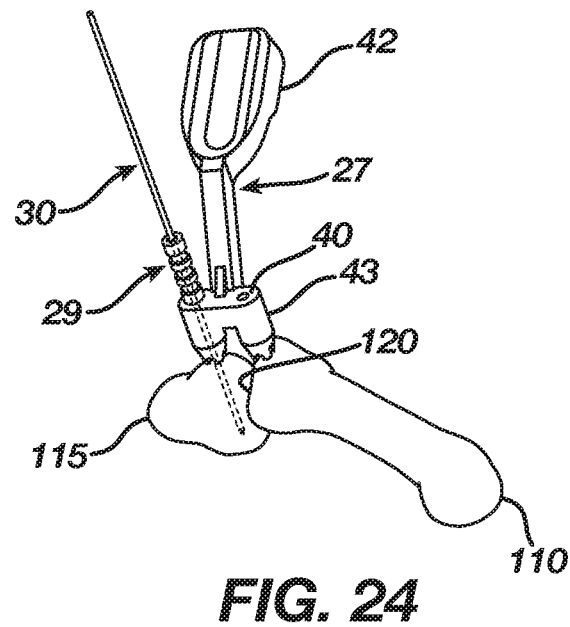
Figure 25:
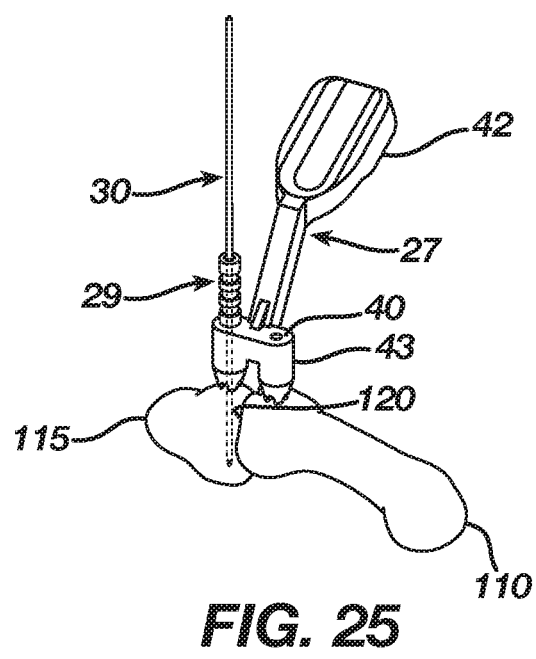

Referring to FIGS. 24 and 25, the surgeon may employ an alternative method to place the first bone 110 and the second bone 115 in their conforming anatomical position prior to retaining the first bone 110 and the second bone 115 in their retained anatomical position using the first and second K-wires 30 in combination with the first and second K-wire guides 29 and the drill guide 27 as illustrated in FIG. 16. The surgeon examines the first bone 110 and the second bone 115 and accordingly selects a drill guide 27 considered by the surgeon to span a fusion site 120 of the first bone 110 and the second bone 115. The surgeon places the selected drill guide 27 atop the first bone 110 and the second bone 115 with the drill guide 27 located across the fusion site 120 whereby the first aperture 40 resides on a first side of the fusion site 120 and the second aperture 41 resides on a second side of the fusion site 120. The surgeon may contour the fusion site 120 of the first bone 110 and the second bone 115 to ensure proper contact of the drill guide 27 with the first bone 110 and the second bone 115. With the drill guide 27 placed atop the first bone 110 and the second bone 115, the surgeon as illustrated in FIG. 24 inserts a first K-wire guide 29 into the second aperture 41 of the drill guide 27. The surgeon then inserts a first K-wire 30 through the cannulation 56 of the first K-wire guide 29 and into the second bone 115. After securing the drill guide 27 with the second bone 115 using the first K-wire guide 29 and the first K-wire 30, the surgeon as illustrated in FIG. 25 manipulates the drill guide 27 to leverage the first bone 110 and the second bone 115 into a conforming anatomical position.

Once the first bone 110 and the second bone 115 reach their conforming anatomical position, the surgeon determines whether the selected drill guide 27 includes a first aperture 40 and a second aperture 41 spaced apart a distance that facilitates implantation across the fusion site 120 and into the first bone 110 and the second bone 115 of an implant 6 having a desired length (i.e., first and second leg 14 and 15 distance in their constrained insertion position). When the surgeon determines the selected drill guide 27 is a correct size, then the surgeon selects an implant 6 with a distance between its first and second legs 14 and 15 when the selected implant 6 resides in its constrained insertion shape 10 and the first and second legs 14 and 15 are located in their constrained insertion position that corresponds with the distance between the first and second apertures 40 and 41 of the selected drill guide 27. The surgeon further verifies whether the conforming anatomical position into which the first bone 110 and the second bone 115 have been leveraged conforms with the predetermined anatomical position using a visual inspection, a measuring tool, fluoroscopy, or the like. If the surgeon determines that the conforming anatomical position conforms with the predetermined anatomical position, then the surgeon inserts a second K-wire guide 29 into the first aperture 40 of the drill guide 27 and a second K-wire 30 through the cannulation 56 of the second K-wire guide 29 and into the first bone 110 such that, as illustrated in FIG. 16, the first and second K-wires 30 in combination with the first and second K-wire guides 29 and the drill guide 27 retain the first bone 110 and the second bone 115 in their retained anatomical position. Conversely, if the surgeon determines that the conforming anatomical position into which the first bone 110 and the second bone 115 have been leveraged does not conform with the predetermined anatomical position, then the surgeon may remove the first K-wire 30 from the first bone 110 and the first K-wire guide 29 as well as the first K-wire guide 29 from the drill guide 27 and the drill guide 27 from the first bone 110 and the second bone 115. This permits the surgeon to again attempt leveraging of the first bone 110 and the second bone 115 into a conforming anatomical position utilizing the drill guide 27, the first K-wire guide 29, and the first K-wire 30 as previously described. After re-leveraging the first bone 110 and the second bone 115 and verifying that the conforming anatomical position conforms with the predetermined anatomical position, the surgeon inserts a second K-wire guide 29 into the first aperture 40 of the drill guide 27 and a second K-wire 30 through the cannulation 56 of the second K-wire guide 29 and into the first bone 110 such that, as illustrated in FIG. 16, the first and second K-wires 30 in combination with the first and second K-wire guides 29 and the drill guide 27 retain the first bone 110 and the second bone 115 in their retained anatomical position.

When the surgeon determines the selected drill guide 27 is not a correct size, then the surgeon may remove the first K-wire 30 from the second bone 115 and the first K-wire guide 29 as well as the first guide 29 from the drill guide 27 and the drill guide 27 from the first bone 110 and the second bone 115. This permits the surgeon to again select a drill guide 27 considered by the surgeon to span the fusion site 120 of the first bone 110 and the second bone 115 followed by the use of the newly selected drill guide 27, the first K-wire guide 29, and the first K-wire 30 to leverage the first bone 110 and the second bone 115 into a conforming anatomical position as previously described. After selecting a correctly sized drill guide 27, the surgeon selects an implant 6 with a distance between its first and second legs 14 and 15 when the selected implant 6 resides in its constrained insertion shape 10 and the first and second legs 14 and 15 are located in their constrained insertion position that corresponds with the distance between the first and second apertures 40 and 41 of the selected drill guide 27. The surgeon further as previously described verifies whether the conforming anatomical position into which the first bone 110 and the second bone 115 have been leveraged conforms with the predetermined anatomical position using a visual inspection, a measuring tool, fluoroscopy, or the like. Once the surgeon as previously described verifies that the conforming anatomical position conforms with the predetermined anatomical position, the surgeon inserts a second K-wire guide 29 into the first aperture 40 of the drill guide 27 and a second first K-wire 30 through the cannulation 56 of the second K-wire guide 29 and into the first bone 110 such that, as illustrated in FIG. 16, the first and second K-wires 30 in combination with the first and second K-wire guides 29 and the drill guide 27 retain the first bone 110 and the second bone 115 in their retained anatomical position.

The foregoing alternative method accordingly results in the first and second K-wires 30 in combination with the first and second K-wire guides 29 and the drill guide 27 as illustrated in FIG. 16 retaining the first bone 110 and the second bone 115 in their retained anatomical position which, in the preferred embodiment, is where the first and second K-wires 30, the first and second K-wire guides 29, and the drill guide 27 hold the first bone 110 and the second bone 115 in their conforming anatomical position. Although the preceding describes the drill guide 27, the first K-wire guide 29, and the first K-wire 30 secured with the second bone 115, one of ordinary skill in the art will recognize that the drill guide 27, the first K-wire guide 29, and the first K-wire 30 may be secured with the first bone 110 in order to permit leveraging of the first bone 110 and the second bone 115 in their conforming anatomical position.

An advantage of the orthopedic fixation system 5 according to the present invention includes leveraging the first bone 110 and the second bone 115 into a conforming anatomical position using the drill guide 27, the first K-wire guide 29, and the first K-wire 30 and then verifying whether the conforming anatomical position corresponds with the predetermined anatomical position prior to an introduction of a second K-wire guide 29 and a second K-wire 30 and an actual drilling of drilled holes. In particular, once the drill guide 27 in combination with the first K-wire 30 and the first K-wire guide 29 leverage the first bone 110 and the second bone 115 into their conformed anatomical position, the surgeon verifies whether the conformed anatomical position conforms with the predetermined anatomical position using a visual inspection, a measuring tool, fluoroscopy, or the like. If the surgeon determines that the conformed anatomical position corresponds with the predetermined anatomical position, then the surgeon may proceed with an introduction of a second K-wire guide 29 and a second K-wire 30 and a drilling of drilled holes. Alternatively, if the surgeon determines that the conformed anatomical position does not correspond with the predetermined anatomical position, then the surgeon may remove the first K-wire 30 from the first bone 110 or the second bone 115 and the first K-wire guide 29 as well as the first K-wire guide 29 from the drill guide 27 and the drill guide 27 from the first bone 110 and the second bone 115. This permits the surgeon to again attempt leveraging of the first bone 110 and the second bone 115 into a conforming anatomical position using the drill guide 27, the first K-wire guide 29, and the first K-wire 30 as previously described. After leveraging the first bone 110 and the second bone 115 results in the first bone 110 and the second bone 115 being positioned in a conforming anatomical position that corresponds with the predetermined anatomical position, the surgeon then may proceed with an introduction of a second K-wire guide 29 and a second K-wire 30 and a drilling of drilled holes. While use of K-wire guides 29 in combination with the drill guide 27 and K-wires 30 enhances the ability of the drill guide 27 and the K-wires 30 to leverage the first bone 110 and the second bone 115 into their conformed anatomical position and then to hold the first bone 110 and the second bone 115 in a retained anatomical position, one of ordinary skill in the art will recognize that the drill guide 27 and the K-wires 30 may be utilized without the benefit of the K-wire guides 29.

Figure 17:
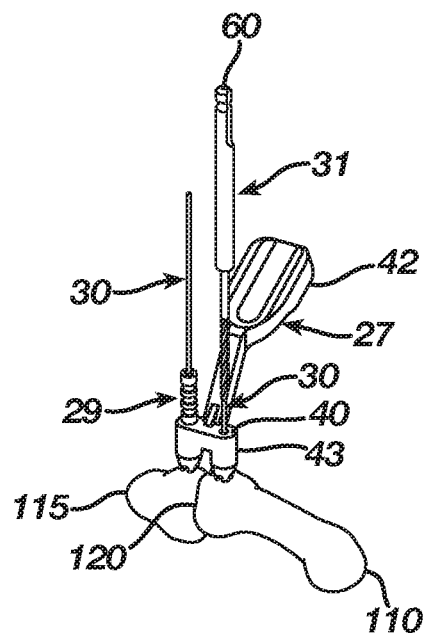
Figure 18:
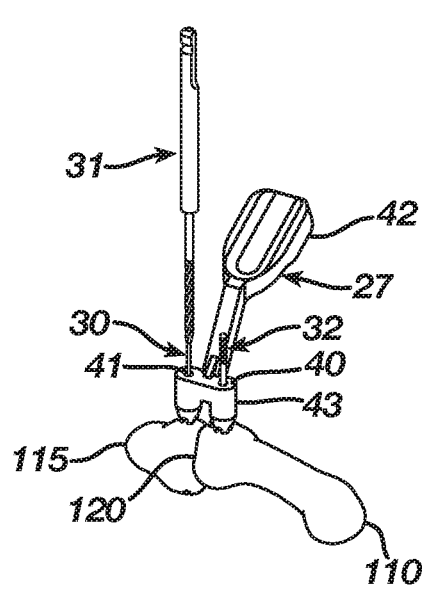

Referring to FIGS. 17 and 18, once the retained anatomical position of the first bone 110 and the second bone 115 corresponds with the predetermined anatomical position for the first bone 110 and the second bone 115, the surgeon drills first and second drilled holes 121 and 122 in the first bone 110 and the second bone 115 using the cannulated drill bit 31. In order to drill the first drilled hole 121, the surgeon removes the first K-wire guide 29 from the drill guide 27 and from over the first K-wire 30 via its cannulation 56. The surgeon then inserts the cannulated drill bit 31 via its cannulation 60 over the first K-wire 30 such that the cutting edge 64 of the cannulated drill bit 31 contacts the first bone 110. The surgeon holds the drill guide 27 against the first bone 110 and then drills over the first K-wire 30 into the first bone 110 until the cannulated drill bit 31 creates the first drilled hole 121 desired by the surgeon, which, in the preferred embodiment, is when the cannulated drill bit 31 contacts a far cortex of the first bone 110, enters the far cortex of the first bone 110, or exits the first bone 110. After drilling the first drilled hole 121, the surgeon removes the cannulated drill bit 31 from over the first K-wire 30 and either leaves the first K-wire 30 or, as illustrated in FIG. 18, removes the first K-wire 30 and inserts a first locating pin 32 through the first aperture 40 of the drill guide 27 and into the first drilled hole 121. The surgeon, in order to drill the second drilled hole 122, removes the second K-wire guide 29 from the drill guide 27 and from over the second K-wire 30 via its cannulation 56. The surgeon then inserts the cannulated drill bit 31 via its cannulation 60 over the second K-wire 30 such that the cutting edge 64 of the cannulated drill bit 31 contacts the second bone 115. The surgeon holds the drill guide 27 against the second bone 115 and then drills over the second K-wire 30 into the second bone 115 until the cannulated drill bit 31 creates the second drilled hole 122 desired by the surgeon, which, in the preferred embodiment, is when the cannulated drill bit 31 contacts a far cortex of the second bone 115, enters the far cortex of the second bone 115, or exits the second bone 115. After drilling the second drilled hole 122, the surgeon removes the cannulated drill bit 31 from over the second K-wire 30 and either leaves the second K-wire 30 or removes the second K-wire 30 and inserts a second locating pin 32 through the second aperture 41 of the drill guide 27 and into the second drilled hole 122. While leaving the first K-wire 30 during the drilling of the second drilled hole 122 adequately retains the first bone 110 and the second bone 115 in their retained anatomical position, a benefit of the first and second locating pins 32 is that increased diameters thereof over the diameters of the first and second K-wires 30 more accurately retain the first bone 110 and the second bone 115 in their retained anatomical position.

An advantage of the orthopedic fixation system 5 according to the present invention includes the first and second K-wires 30 and the drill guide 27 in combination with the cannulated drill bit 31 facilitating precise drilling of the first and second drilled holes 121 and 122 into the first bone 110 and the second bone 115. In particular, as previously described, the first and second K-wires 30 and the drill guide 27 retain the first bone 110 and the second bone 115 in their retained anatomical position during the drilling of the first and second drilled holes 121 and 122. Moreover, the cannulated drill bit 31, due to its cannulation 60, installs over the first and second K-wires 30 such that the cannulated drill bit 31 drills the first and second drilled holes 121 and 122 while first bone 110 and the second bone 115 is held in a retained anatomical position and thus a conforming anatomical position corresponding with a predetermined anatomical position that desirable to promote a fusion and thus a healing of the first bone 110 and the second bone 115.

The surgeon may create a trough, in line with the first and second drilled holes 121 and 122, that permits the implant 6 to be recessed within the first bone 110 and the second bone 115. The surgeon removes the first or second K-wires 30 or the first and second locating pins 32 and then uses an instrument such as rongeurs to form the trough that lowers the location of the bridge 11 for the implant 6 relative to the first bone 110 and the second bone 115.

Figure 19:
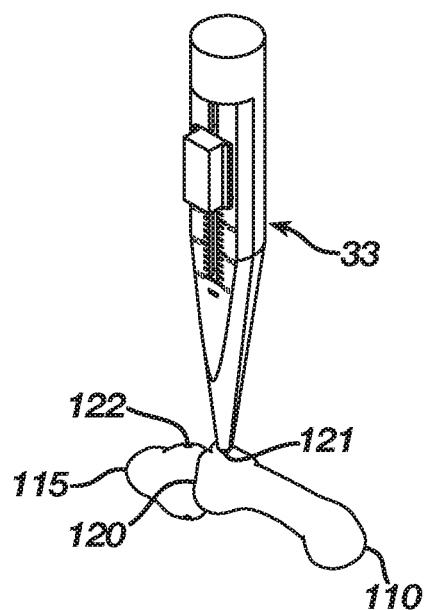

Referring to FIG. 19, the surgeon, after removal of the first or second K-wires 30 or the first and second locating pins 32, uses the depth gauge 33 to determine the depths of the first and second drilled holes 121 and 122 in the first bone 110 and the second bone 115. The surgeon places the depth gauge 33 abutting the first bone 110 and over the first drilled hole 121 therein. The surgeon extends the rod 73 of the depth gauge 33 into the first drilled hole 121 using its slider 72 until the rod 73 contacts the end of the first drilled hole 121 or the rod 73 resides at the exit of the first drilled hole 121 from the first bone 110 with its hooks 74 engaging the first bone 110. The surgeon reads the location of the slider 72 along the scale 71 of the depth gauge 33 thereby obtaining the depth of the first drilled hole 121. The surgeon removes the depth gauge 33 from the drilled hole 121 and then employs the depth gauge 33 to read the depth of the second drilled hole 122. Once the depths of the first and second drilled holes 121 and 122 are determined, the surgeon selects an implant 6 with first and second legs 14 and 15 having lengths corresponding to the depths of the first and second drilled holes 121 and 122.

Figure 20:
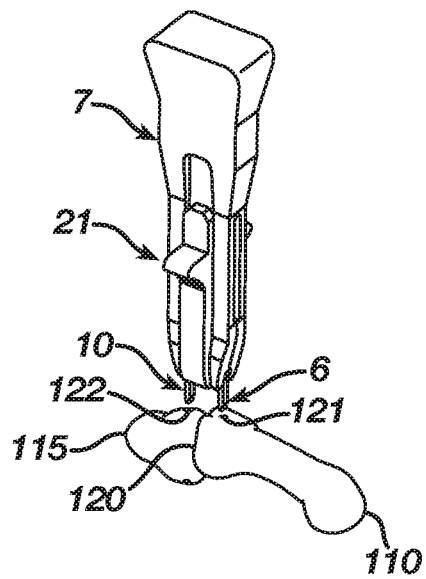
Figure 21:
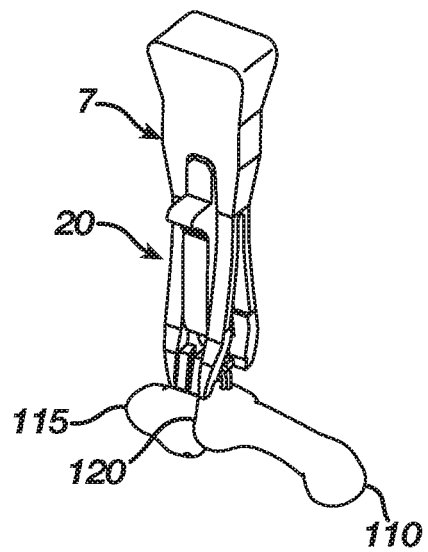

Referring to FIGS. 20 and 21, the surgeon, if necessary, manipulates the first bone 110 and the second bone 115 to re-align the first and second drilled holes 121 and 122, thereby ensuring the first bone 110 and the second bone 115 reside in their conforming anatomical position and thus their predetermined anatomical position. The surgeon utilizes the implant insertion device 7 to position and then implant the implant 6 into the first bone 110 and the second bone 115. In particular, the surgeon utilizes the implant insertion device 7 to position the tip 16 of the first leg 14 for the implant 6 at the first drilled hole 121 and the tip 17 of the second leg 15 for the implant 6 at the second drilled hole 122. The surgeon then inserts the first leg 14 into the drilled hole 121 and the second leg 15 into the second drilled hole 122. Once the first and second legs 14 and 15 insert, respectively, into the first and second drilled hole 121 and 122, the implant 6 is ready for removal from the implant insertion device 7. To remove the implant 6 from the implant insertion device 7, the surgeon moves the implant insertion device 7 from its implant engagement position 21 to its implant disengagement position 20, resulting in the implant 6 being released from the implant insertion device 7. The surgeon accordingly removes the implant insertion device 7 from the implant 6 thereby leaving the implant 6 within the first bone 110 and the second bone 115 as illustrated in FIG. 21.

Figure 22:
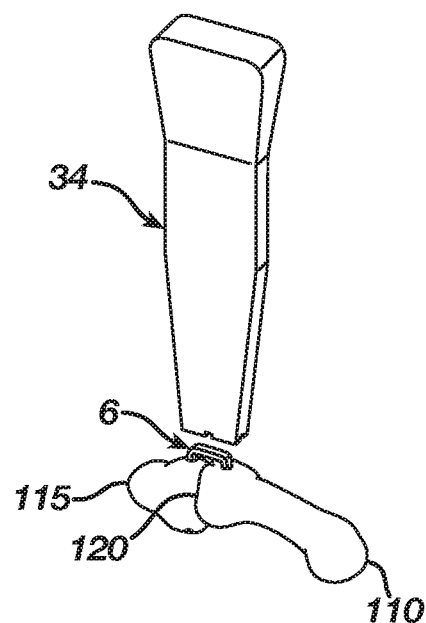

Referring to FIG. 22, the surgeon, after disengaging the implant insertion device 7 from the implant 6, utilizes the tamp 29 to tamp the implant 6 in abutting relationship with first bone 110 and the second bone 115. The surgeon engages the bridge 11 of the implant 6 with the implant engagement end 76 of the tamp 34 and then, once engaged therewith, pushes the implant 6 to its implanted position abutting the first bone 110 and the second bone 115.

Figure 23:
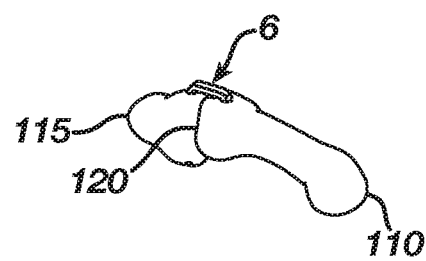

Referring to FIG. 23, with the implant 6 implanted into the first bone 110 and the second bone 115, the implant 6 attempts to transition from its constrained insertion shape 10 to its unconstrained shape 9 such that the implant 6 through its continuous compression of the first bone 110 and the second bone 115 remains implanted in the first bone 110 and the second bone 115 thereby holding the first bone 110 and the second bone 115 in their predetermined anatomical position and assisting in the fusing thereof. In particular, the first and second legs 14 and 15 of the implant 6 attempt to move from their constrained insertion position to their unconstrained position such that the implant 6 delivers the energy stored in the transition sections 18 and 19 to the first bone 110 and the second bone 115, thereby exerting a compressive force to the first bone 110 and the second bone 115 that assists in the fusing and thus the healing thereof.

Points of the Invention:

1. A method for an orthopedic fixation system, comprising:
    (i) determining a predetermined anatomical position for a first bone and a second bone;
    (ii) selecting a drill guide from a plurality of drill guides, whereby each drill guide includes a first aperture residing at a preset distance from a second aperture, further whereby each preset distance is different;
    (iii) placing the drill guide atop the first bone and the second bone with the drill guide located across the fusion site whereby the first aperture of the drill guide is located at the first bone and the second aperture of the drill guide is located across the fusion site at the second bone;
    (iv) inserting a first K-wire through the first aperture of the drill guide and into the first bone;
    (v) manipulating the drill guide to leverage the first bone and the second bone into a conforming anatomical position that corresponds with the predetermined anatomical position;
    (vi) inserting a second K-wire through the second aperture of the drill guide and into the second bone such that the first and second K-wires and the drill guide retain the first bone and the second bone in a retained anatomical position that corresponds with the predetermined anatomical position;
    (vii) selecting an implant including an unconstrained shape and a constrained insertion shape that corresponds with the preset distance between the first and second apertures of the drill guide;
    (viii) inserting a cannulated drill bit via a cannulation thereof over the first K-wire such that the cannulated drill bit contacts the first bone;
    (ix) drilling over the first K-wire into the first bone until the cannulated drill bit creates a first drilled hole;
    (x) removing the cannulated drill bit from over the first K-wire;
    (xi) inserting the cannulated drill bit via its cannulation over the second K-wire such that the cannulated drill bit contacts the second bone;
    (xii) drilling over the second K-wire into the second bone until the cannulated drill bit creates a second drilled hole;
    (xiii) removing the cannulated drill bit from over the second K-wire;
    (xiv) removing the drill guide from over the first and second K-wires;
    (xv) removing the first K-wire from the first drilled hole and the second K-wire from the second drilled hole;
    (xvi) inserting the implant into the first drilled hole and the second drilled hole whereby the implant attempts to transition from its constrained insertion shape to its unconstrained shape such that the implant continuously compresses the first bone and the second bone thereby holding the first bone and the second bone in the predetermined anatomical position.

2. The method for an orthopedic fixation system as in 1, wherein, after step (v) and prior to step (vi), determining whether the drill guide is a correct size, whereby the drill guide is a correct size when the preset distance between the first aperture and the second aperture spaces apart the first and second apertures across the fusion site of the first bone and the second bone a desired distance for implantation of an implant into the first bone and the second bone, further whereby, when the drill guide is an incorrect size:

removing the first K-wire from the first aperture of the drill guide and the drill guide from atop the first bone and the second bone,
repeating steps (ii)-(v), and
determining whether the drill guide is a correct size.

3. The method for an orthopedic fixation system as in 1, wherein, after step (v) and prior to step (vi), verifying whether the conforming anatomical position corresponds with the predetermined anatomical position, whereby, when the conforming anatomical position does not correspond with the predetermined anatomical position:
removing the first K-wire from the first aperture of the drill guide and the drill guide from atop the first bone and the second bone, and
repeating steps (iii)-(v), and
verifying whether the conforming anatomical position corresponds with the predetermined anatomical position.

4. The method for an orthopedic fixation system as in 1, further comprising:
inserting a first K-wire guide into the first aperture of the drill guide prior to the first K-wire, whereby the first K-wire guide includes a cannulation sized to receive the first K-wire therethrough, further whereby the first K-wire guide stabilizes the first K-wire within the first aperture of the drill guide; and
removing the first K-wire guide from the drill guide and from over the first K-wire prior to inserting a cannulated drill bit over the first K-wire and removing the first K-wire from the first bone.

5. The method for an orthopedic fixation system as in 4, further comprising:
inserting a second K-wire guide into the second aperture of the drill guide prior to the second K-wire, whereby the second K-wire guide includes a cannulation sized to receive the second K-wire therethrough, further whereby the second K-wire guide stabilizes the second K-wire within the second aperture of the drill guide; and
removing the second K-wire guide from the drill guide and from over the second K-wire prior to inserting a cannulated drill bit over the second K-wire and removing the second K-wire from the second bone.

6. The method for an orthopedic fixation system as in 1, wherein selecting an implant in step (vi), comprises:
providing a plurality of implants, each implant comprising a first leg and a second leg with a bridge therebetween, whereby:
the first and second legs are spaced apart at a first distance when the implant resides in an unconstrained shape and the first and second legs are spaced apart at a second distance when the implant resides in a constrained insertion shape,
each of the first distances for the first and second legs of the implants is different, and
each of the second distances for the first and second legs of the implants is different; and
selecting an implant from the plurality of implants, whereby the second distance of the first and second legs for the selected implant corresponds with the preset distance between the first and second apertures of the drill guide.

7. The method for an orthopedic fixation system as in 6, wherein inserting the implant (xvi), comprises inserting the first leg of the implant into the first drilled hole and the second leg of the implant into the second drilled hole whereby the implant attempts to transition from its constrained insertion shape to its unconstrained shape such that the implant continuously compresses the first bone and the second bone thereby holding the first bone and the second bone in the predetermined anatomical position.

8. The method for an orthopedic fixation system as in 1, wherein, after step (x) and prior to step (xi):
removing the first K-wire from the first drilled hole of the first bone and the first aperture of the drill guide; and
inserting a first locating pin through the first aperture of the drill guide and into the first drilled hole of the first bone.

9. The method for an orthopedic fixation system as in 8, wherein, after step (xiii) and prior to step (xiv):
removing the second K-wire from the second drilled hole of the second bone and the second aperture of the drill guide; and
inserting a second locating pin through the second aperture of the drill guide and into the second drilled hole of the second bone.

10. The method for an orthopedic fixation system as in 9, wherein, in place of steps (xiv) and (xv):
removing the drill guide from over the first and second locating pins; and
removing the first locating pin from the first drilled hole and second locating pin from the second drilled hole.

11. The method for an orthopedic fixation system as in 6 wherein, after step (xv) and prior to step (xvi), determining a depth of the first and second drilled holes to permit selection of an implant with first and second legs having a length corresponding with the depth of the first and second drilled holes.

12. The method for an orthopedic fixation system as in 7, wherein, after step (xvi), tamping the implant to an implanted position whereby the first leg resides within the first drilled hole, the second leg resides in the second drilled hole, and the bridge abuts the first bone and the second bone across the fusion site thereof.

13. A method for an orthopedic fixation system, comprising:
(i) determining a predetermined anatomical position for a first bone and a second bone;
(ii) selecting a drill guide from a plurality of drill guides, whereby each drill guide includes a first aperture residing at a preset distance from a second aperture, further whereby each preset distance is different;
(iii) placing the drill guide atop the first bone and the second bone such that the drill guide spans a fusion site of the first bone and the second bone, whereby the first aperture of the drill guide is located at the first bone and the second aperture of the drill guide is located across the fusion site at the second bone;
(iv) inserting a first K-wire through the first aperture of the drill guide and into the first bone;
(v) manipulating the drill guide to leverage the first bone and the second bone into a conforming anatomical position;
(vi) determining whether the drill guide is a correct size, whereby the drill guide is a correct size when the preset distance between the first aperture and the second aperture spaces apart the first and second apertures across the fusion site of the first bone and the second bone a desired distance for implantation of an implant into the first bone and the second bone, further whereby, when the drill guide is an incorrect size:
removing the first K-wire from the first aperture of the drill guide and the drill guide from atop the first bone and the second bone, and
repeating steps (ii)-(vi) until the drill guide is a correct size;
(vii) verifying whether the conforming anatomical position corresponds with the predetermined anatomical position, whereby, when the conforming anatomical position does not correspond with the predetermined anatomical position:
removing the first K-wire from the first aperture of the drill guide and the drill guide from atop the first bone and the second bone, and
repeating steps (iii)-(vi) and (vii) until the conforming anatomical position corresponds with the predetermined anatomical position:
(viii) inserting a second K-wire through the second aperture of the drill guide and into the second bone such that the first and second K-wires and the drill guide retain the first bone and the second bone in a retained anatomical position that corresponds with the predetermined anatomical position;
(ix) selecting an implant including an unconstrained shape and a constrained insertion shape that corresponds with the preset distance between the first and second apertures of the drill guide;
(x) inserting a cannulated drill bit via a cannulation thereof over the first K-wire such that the cannulated drill bit contacts the first bone;
(xi) drilling over the first K-wire into the first bone until the cannulated drill bit creates a first drilled hole;
(xii) removing the cannulated drill bit from over the first K-wire;
(xiii) inserting the cannulated drill bit via its cannulation over the second K-wire such that the cannulated drill bit contacts the second bone;
(xiv) drilling over the second K-wire into the second bone until the cannulated drill bit creates a second drilled hole;
(xv) removing the cannulated drill bit from over the second K-wire;
(xvi) removing the drill guide from over the first and second K-wires;
(xvii) removing the first K-wire from the first drilled hole and the second K-wire from the second drilled hole;
(xviii) inserting the implant into the first drilled hole and the second drilled hole whereby the implant attempts to transition from its constrained insertion shape to its unconstrained shape such that the implant continuously compresses the first bone and the second bone thereby holding the first bone and the second bone in the predetermined anatomical position.

14. The method for an orthopedic fixation system as in 13, further comprising:
inserting a first K-wire guide into the first aperture of the drill guide prior to the first K-wire, whereby the first K-wire guide includes a cannulation sized to receive the first K-wire therethrough, further whereby the first K-wire guide stabilizes the first K-wire within the first aperture of the drill guide; and
removing the first K-wire guide from the drill guide and from over the first K-wire prior to inserting a cannulated drill bit over the first K-wire and removing the first K-wire from the first bone.

15. The method for an orthopedic fixation system as in 14 41, further comprising:
inserting a second K-wire guide into the second aperture of the drill guide prior to the second K-wire, whereby the second K-wire guide includes a cannulation sized to receive the second K-wire therethrough, further whereby the second K-wire guide stabilizes the second K-wire within the second aperture of the drill guide; and
removing the second K-wire guide from the drill guide and from over the second K-wire prior to inserting a cannulated drill bit over the second K-wire and removing the second K-wire from the second bone.

16. The method for an orthopedic fixation system as in 13, wherein selecting an implant in step (ix), comprises:
providing a plurality of implants, each implant comprising a first leg and a second leg with a bridge therebetween, whereby:
the first and second legs are spaced apart at a first distance when the implant resides in an unconstrained shape and the first and second legs are spaced apart at a second distance when the implant resides in a constrained insertion shape,
each of the first distances for the first and second legs of the implants is different, and
each of the second distances for the first and second legs of the implants is different; and
selecting an implant from the plurality of implants, whereby the second distance of the first and second legs for the selected implant corresponds with the preset distance between the first and second apertures of the drill guide.

17. The method for an orthopedic fixation system as in 16, wherein inserting the implant (xviii), comprises inserting the first leg of the implant into the first drilled hole and the second leg of the implant into the second drilled hole whereby the implant attempts to transition from its constrained insertion shape to its unconstrained shape such that the implant continuously compresses the first bone and the second bone thereby holding the first bone and the second bone in the predetermined anatomical position.

18. The method for an orthopedic fixation system as in 13, wherein, after step (xii) and prior to step (xiii):
removing the first K-wire from the first drilled hole of the first bone and the first aperture of the drill guide; and
inserting a first locating pin through the first aperture of the drill guide and into the first drilled hole of the first bone.

19. The method for an orthopedic fixation system as in 18, wherein, after step (xv) and prior to step (xvi):
removing the second K-wire from the second drilled hole of the second bone and the second aperture of the drill guide; and
inserting a second locating pin through the second aperture of the drill guide and into the second drilled hole of the second bone.

20. The method for an orthopedic fixation system as in 19, wherein, in place of steps (xvi) and (xvii):
removing the drill guide from over the first and second locating pins; and
removing the first locating pin from the first drilled hole and second locating pin from the second drilled hole.

21. The method for an orthopedic fixation system as in 16 wherein, after step (xvii) and prior to step (xviii), determining a depth of the first and second drilled holes to permit selection of an implant with first and second legs having a length corresponding with the depth of the first and second drilled holes.

22. The method for an orthopedic fixation system as in 17, wherein, after step (xviii), tamping the implant to an implanted position whereby the first leg resides within the first drilled hole, the second leg resides in the second drilled hole, and the bridge abuts the first bone and the second bone across the fusion site thereof.

23. A method for an orthopedic fixation system, comprising:
(i) providing a plurality of implants, each implant comprising a first leg and a second leg with a bridge therebetween, whereby:
the first and second legs are spaced apart at a first distance when the implant resides in an unconstrained shape and the first and second legs are spaced apart at a second distance when the implant resides in a constrained insertion shape, each of the first distances for the first and second legs of the implants is different, and each of the second distances for the first and second legs of the implants is different;

(ii) providing a sizing guide including a body that defines at a perimeter thereof a plurality of fixed distances corresponding with the second distance between the first leg and the second leg of one of the plurality of implants in its constrained insertion shape;

(iii) determining a predetermined anatomical position for a first bone and a second bone;

(iv) manipulating the first bone and the second bone into a conforming anatomical position that corresponds with the predetermined anatomical position;

(v) sequentially positioning the fixed distances of the sizing guide across a fusion site of the first bone and the second bone until a fixed distance indicates a desired distance across the first bone and the second bone for implantation of an implant into the first bone and the second bone;

(vi) selecting an implant from the plurality of implants with a second distance between its first and second legs corresponding with the fixed distance of the sizing guide indicating the desired distance;

(vii) selecting a drill guide from a plurality of drill guides with a preset distance between a first aperture and a second aperture corresponding with the second distance between the first and second legs of the selected implant;

(viii) placing the drill guide atop the first bone and the second bone with the drill guide located across the fusion site whereby the first aperture of the drill guide is located at the first bone and the second aperture of the drill guide is located across the fusion site at the second bone;

(ix) inserting a first K-wire through the first aperture of the drill guide and into the first bone;

(x) inserting a second K-wire through the second aperture of the drill guide and into the second bone such that the first and second K-wires and the drill guide retain the first bone and the second bone in a retained anatomical position that corresponds with the predetermined anatomical position;

(xi) inserting a cannulated drill bit via a cannulation thereof over the first K-wire such that the cannulated drill bit contacts the first bone;

(xii) drilling over the first K-wire into the first bone until the cannulated drill bit creates a first drilled hole;

(xiii) removing the cannulated drill bit from over the first K-wire;

(xiv) inserting the cannulated drill bit via its cannulation over the second K-wire such that the cannulated drill bit contacts the second bone;

(xv) drilling over the second K-wire into the second bone until the cannulated drill bit creates a second drilled hole;

(xvi) removing the cannulated drill bit from over the second K-wire;

(xvii) removing the drill guide from over the first and second K-wires;

(xviii) removing the first K-wire from the first drilled hole and the second K-wire from the second drilled hole;

(xix) inserting the first leg of the implant into the first drilled hole and the second leg of the implant into the second drilled hole whereby the implant attempts to transition from its constrained insertion shape to its unconstrained shape such that the implant continuously compresses the first bone and the second bone thereby holding the first bone and the second bone in the predetermined anatomical position.

24. The method for an orthopedic fixation system as in 23, wherein, after step (x) and prior to step (xi), verifying whether the retained anatomical position corresponds with the predetermined anatomical position, whereby, when the retained anatomical position does not correspond with the predetermined anatomical position:

removing the first K-wire from the first aperture of the drill guide, the second K-wire from the second aperture of the drill guide, and the drill guide from atop the first bone and the second bone, manipulating the first bone and the second bone into a conforming anatomical position that corresponds with the predetermined anatomical position, and repeating steps (viii)-(x), and verifying whether the retained anatomical position corresponds with the predetermined anatomical position.

25. The method for an orthopedic fixation system as in 23, further comprising:

inserting a first K-wire guide into the first aperture of the drill guide prior to the first K-wire, whereby the first K-wire guide includes a cannulation sized to receive the first K-wire therethrough, further whereby the first K-wire guide stabilizes the first K-wire within the first aperture of the drill guide; and removing the first K-wire guide from the drill guide and from over the first K-wire prior to inserting a cannulated drill bit over the first K-wire and removing the first K-wire from the first bone.

26. The method for an orthopedic fixation system as in 25, further comprising:

inserting a second K-wire guide into the second aperture of the drill guide prior to the second K-wire, whereby the second K-wire guide includes a cannulation sized to receive the second K-wire therethrough, further whereby the second K-wire guide stabilizes the second K-wire within the second aperture of the drill guide; and removing the second K-wire guide from the drill guide and from over the second K-wire prior to inserting a cannulated drill bit over the second K-wire and removing the second K-wire from the second bone.

27. The method for an orthopedic fixation system as in 23, wherein, after step (xiii) and prior to step (xiv):

removing the first K-wire from the first drilled hole of the first bone and the first aperture of the drill guide; and inserting a first locating pin through the first aperture of the drill guide and into the first drilled hole of the first bone.

28. The method for an orthopedic fixation system as in 27, wherein, after step (xvi) and prior to step (xvii):

removing the second K-wire from the second drilled hole of the second bone and the second aperture of the drill guide; and inserting a second locating pin through the second aperture of the drill guide and into the second drilled hole of the second bone.

29. The method for an orthopedic fixation system as in 28, wherein, in place of steps (xvii) and (xviii):

removing the drill guide from over the first and second locating pins; and removing the first locating pin from the first drilled hole and the second locating pin from the second drilled hole.

30. The method for an orthopedic fixation system as in 23 wherein, after step (xviii) and prior to step (xix), determining a depth of the first and second drilled holes to permit selection of an implant with first and second legs having a length corresponding with the depth of the first and second drilled holes.

31. The method for an orthopedic fixation system as in 23, wherein, after step (xix), tamping the implant to an implanted position whereby the first leg resides within the first drilled hole, the second leg resides in the second drilled hole, and the bridge abuts the first bone and the second bone across the fusion site thereof.

32. A method for an orthopedic fixation system, comprising:
  (i) providing a plurality of implants, each implant comprising a first leg and a second leg with a bridge therebetween, whereby:
    the first and second legs are spaced apart at a first distance when the implant resides in an unconstrained shape and the first and second legs are spaced apart at a second distance when the implant resides in a constrained insertion shape,
    each of the first distances for the first and second legs of the implants is different, and
    each of the second distances for the first and second legs of the implants is different;
  (ii) providing a sizing guide including a body that defines at a perimeter thereof a plurality of fixed distances corresponding with the second distance between the first leg and the second leg of one of the plurality of implants in its constrained insertion shape;
  (iii) determining a predetermined anatomical position for a first bone and a second bone;
  (iv) manipulating the first bone and the second bone into a conforming anatomical position that corresponds with the predetermined anatomical position;
  (v) sequentially positioning the fixed distances of the sizing guide across a fusion site of the first bone and the second bone until a fixed distance indicates a desired distance across the first bone and the second bone for implantation of an implant into the first bone and the second bone;
  (vi) selecting an implant from the plurality of implants with a second distance between its first and second legs corresponding with the fixed distance of the sizing guide indicating the desired distance;
  (vii) selecting a drill guide from a plurality of drill guides with a preset distance between a first aperture and a second aperture corresponding with the second distance between the first and second legs of the selected implant;
  (viii) placing the drill guide atop the first bone and the second bone with the drill guide located across the fusion site whereby the first aperture of the drill guide is located at the first bone and the second aperture of the drill guide is located across the fusion site at the second bone;
  (ix) inserting a first K-wire through the first aperture of the drill guide and into the first bone;
  (x) inserting a second K-wire through the second aperture of the drill guide and into the second bone such that the first and second K-wires and the drill guide retain the first bone and the second bone in a retained anatomical position;
  (xi) verifying whether the retained anatomical position corresponds with the predetermined anatomical position, whereby, when the retained anatomical position does not correspond with the predetermined anatomical position:
    removing the first K-wire from the first aperture of the drill guide, the second K-wire from the second aperture of the drill guide, and the drill guide from atop the first bone and the second bone,
    manipulating the first bone and the second bone into a conforming anatomical position that corresponds with the predetermined anatomical position, and
    repeating steps (viii)-(xi) until the retained anatomical position corresponds with the predetermined anatomical position;
  (xii) inserting a cannulated drill bit via a cannulation thereof over the first K-wire such that the cannulated drill bit contacts the first bone;
  (xiii) drilling over the first K-wire into the first bone until the cannulated drill bit creates a first drilled hole;
  (xiv) removing the cannulated drill bit from over the first K-wire;
  (xv) inserting the cannulated drill bit via its cannulation over the second K-wire such that the cannulated drill bit contacts the second bone;
  (xvi) drilling over the second K-wire into the second bone until the cannulated drill bit creates a second drilled hole;
  (xvii) removing the cannulated drill bit from over the second K-wire;
  (xviii) removing the drill guide from over the first and second K-wires;
  (xix) removing the first K-wire from the first drilled hole and the second K-wire from the second drilled hole;
  (xx) inserting the first leg of the implant into the first drilled hole and the second leg of the implant into the second drilled hole whereby the implant attempts to transition from its constrained insertion shape to its unconstrained shape such that the implant continuously compresses the first bone and the second bone thereby holding the first bone and the second bone in the predetermined anatomical position.

33. The method for an orthopedic fixation system as in 32, further comprising:
  inserting a first K-wire guide into the first aperture of the drill guide prior to the first K-wire, whereby the first K-wire guide includes a cannulation sized to receive the first K-wire therethrough, further whereby the first K-wire guide stabilizes the first K-wire within the first aperture of the drill guide; and
  removing the first K-wire guide from the drill guide and from over the first K-wire prior to inserting a cannulated drill bit over the first K-wire and removing the first K-wire from the first bone.

34. The method for an orthopedic fixation system as in 33, further comprising:
  inserting a second K-wire guide into the second aperture of the drill guide prior to the second K-wire, whereby the second K-wire guide includes a cannulation sized to receive the second K-wire therethrough, further whereby the second K-wire guide stabilizes the second K-wire within the second aperture of the drill guide; and
  removing the second K-wire guide from the drill guide and from over the second K-wire prior to inserting a cannulated drill bit over the second K-wire and removing the second K-wire from the second bone.

35. The method for an orthopedic fixation system as in 32, wherein, after step (xiii) and prior to step (xiv):
  removing the first K-wire from the first drilled hole of the first bone and the first aperture of the drill guide; and
  inserting a first locating pin through the first aperture of the drill guide and into the first drilled hole of the first bone.

36. The method for an orthopedic fixation system as in 35, wherein, after step (xvi) and prior to step (xvii):
  removing the second K-wire from the second drilled hole of the second bone and the second aperture of the drill guide; and
  inserting a second locating pin through the second aperture of the drill guide and into the second drilled hole of the second bone.

37. The method for an orthopedic fixation system as in 36, wherein, in place of steps (xvii) and (xviii):
  removing the drill guide from over the first and second locating pins; and removing the first locating pin from the first drilled hole and the second locating pin from the second drilled hole.

38. The method for an orthopedic fixation system as in 32 wherein, after step (xviii) and prior to step (xix), determining a depth of the first and second drilled holes to permit selection of an implant with first and second legs having a length corresponding with the depth of the first and second drilled holes.

39. The method for an orthopedic fixation system as in 32, wherein, after step (xix), tamping the implant to an implanted position whereby the first leg resides within the first drilled hole, the second leg resides in the second drilled hole, and the bridge abuts the first bone and the second bone across the fusion site thereof.

Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. An orthopedic fixation system for fusing a first bone and a second bone in a predetermined anatomical position, comprising:
    an implant adapted to transition between an unconstrained shape and a constrained insertion shape;
    an implant insertion device adapted to constrain the implant in its constrained insertion shape;
    a drill guide including a first aperture and a second aperture therethrough that are spaced apart a preset distance corresponding with the implant in its constrained insertion shape;
    first and second K-wires;
    a cannulated drill bit;
    the drill guide adapted to reside atop the first bone and the second bone across a fusion site thereof, whereby the first aperture of the drill guide is located at the first bone and the second aperture of the drill guide is located across the fusion site at the second bone;
    the first K-wire adapted to insert through the first aperture of the drill guide and into the first bone, whereby manipulation of the drill guide leverages the first bone and the second bone into a conforming anatomical position, further whereby the first K-wire and the drill guide hold the first bone and the second bone to permit a verification of whether the conforming anatomical position corresponds with the predetermined anatomical position;
    the second K-wire adapted to insert through the second aperture of the drill guide and into the second bone, whereby the first and second K-wires and the drill guide hold the first bone and the second bone in a retained anatomical position that corresponds with the predetermined anatomical position;
    the cannulated drill bit adapted to fit over the first K-wire and to drill into the first bone until the cannulated drill bit creates a first drilled hole;
    the cannulated drill bit adapted to fit over the second K-wire and to drill into the second bone until the cannulated drill bit creates a second drilled hole; and
    the implant insertion device adapted to insert the implant into the first drilled hole and the second drilled hole whereby, after release of the implant from the implant insertion device, the implant attempts to transition from its constrained insertion shape to its unconstrained shape such that the implant continuously compresses the first bone and the second bone thereby holding the first bone and the second bone in the predetermined anatomical position.

2. The orthopedic fixation system according to claim 1, comprising:
    a first K-wire guide adapted to engage the drill guide at its first aperture, the first K-wire guide including a cannulation sized to receive the first K-wire therethrough, whereby the first K-wire guide stabilizes the first K-wire within the first aperture of the drill guide; and
    a second K-wire guide adapted to engage the drill guide at its second aperture, the second K-wire guide including a cannulation sized to receive the second K-wire therethrough, whereby the second K-wire guide stabilizes the second K-wire within the second aperture of the drill guide.

3. The orthopedic fixation system according to claim 1, the implant, comprising a first leg and a second leg with a bridge therebetween whereby the first and second legs are spaced apart at a first distance when the implant resides in its unconstrained shape and the first and second legs are spaced apart at a second distance when the implant resides in its constrained insertion shape.

4. The orthopedic fixation system according to claim 3, wherein the preset distance between the first aperture and the second aperture corresponds with second distance between the first and second legs when the implant resides in its constrained insertion shape.

5. The orthopedic fixation system according to claim 1, comprising a sizing guide including a body that defines at a perimeter thereof at least one fixed distance corresponding with the preset distance between the first aperture and the second aperture of the drill guide.

6. The orthopedic fixation system according to claim 1, comprising:
    a first locating pin insertable into the first drilled hole of the first bone to locate the first drilled hole, the first locating pin adapted to insert through the first aperture of the drill guide;
    a second locating pin insertable into the second drilled hole of the second bone to locate the second drilled hole, the second locating pin adapted to insert through the second aperture of the drill guide; and
    the first and second locating pins and the drill guide hold the first bone and the second bone in a retained anatomical position that corresponds with the predetermined anatomical position.

7. The orthopedic fixation system according to claim 3, comprising a depth gauge adapted to determine a depth of the first and second drilled holes to permit selection of an implant with first and second legs having a length corresponding with the depth of the first and second drilled holes.

8. The orthopedic fixation system according to claim 3, comprising a tamp adapted to tamp an implant to an implanted position whereby the first leg resides within the first drilled hole, the second leg resides in the second drilled hole, and the bridge abuts the first bone and the second bone across the fusion site thereof.

9. An orthopedic fixation system for fusing a first bone and a second bone in a predetermined anatomical position, comprising:
    an implant adapted to transition between an unconstrained shape and a constrained insertion shape;
    an implant insertion device adapted to constrain the implant in its constrained insertion shape;

a drill guide including a first aperture and a second aperture therethrough that are spaced apart a preset distance corresponding with the implant in its constrained insertion shape;

first and second K-wires;

a cannulated drill bit;

the drill guide adapted to reside atop the first bone and the second bone across a fusion site thereof once the first bone and the second bone reside in a conforming anatomical position that corresponds with the predetermined anatomical position, whereby the first aperture of the drill guide is located at the first bone and the second aperture of the drill guide is located across the fusion site at the second bone;

the first K-wire adapted to insert through the first aperture of the drill guide and into the first bone;

the second K-wire adapted to insert through the second aperture of the drill guide and into the second bone, whereby the first and second K-wires and the drill guide hold the first bone and the second bone in a retained anatomical position that permits a verification of whether the conforming anatomical position corresponds with the predetermined anatomical position;

the cannulated drill bit adapted to fit over the first K-wire and to drill into the first bone until the cannulated drill bit creates a first drilled hole;

the cannulated drill bit adapted to fit over the second K-wire and to drill into the second bone until the cannulated drill bit creates a second drilled hole; and the implant insertion device adapted to insert the implant into the first drilled hole and the second drilled hole whereby, after release of the implant from the implant insertion device, the implant attempts to transition from its constrained insertion shape to its unconstrained shape such that the implant continuously compresses the first bone and the second bone thereby holding the first bone and the second bone in the predetermined anatomical position.

10. The orthopedic fixation system according to claim 9, comprising:

a first K-wire guide adapted to engage the drill guide at its first aperture, the first K-wire guide including a cannulation sized to receive the first K-wire therethrough, whereby the first K-wire guide stabilizes the first K-wire within the first aperture of the drill guide; and a second K-wire guide adapted to engage the drill guide at its second aperture, the second K-wire guide including a cannulation sized to receive the second K-wire therethrough, whereby the second K-wire guide stabilizes the second K-wire within the second aperture of the drill guide.

11. The orthopedic fixation system according to claim 9, the implant, comprising a first leg and a second leg with a bridge therebetween whereby the first and second legs are spaced apart at a first distance when the implant resides in its unconstrained shape and the first and second legs are spaced apart at a second distance when the implant resides in its constrained insertion shape.

12. The orthopedic fixation system according to claim 11, wherein the preset distance between the first aperture and the second aperture corresponds with second distance between the first and second legs when the implant resides in its constrained insertion shape.

13. The orthopedic fixation system according to claim 9, comprising a sizing guide including a body that defines at a perimeter thereof at least one fixed distance corresponding with the preset distance between the first aperture and the second aperture of the drill guide.

14. The orthopedic fixation system according to claim 9, comprising:

a first locating pin insertable into the first drilled hole of the first bone to locate the first drilled hole, the first locating pin adapted to insert through the first aperture of the drill guide;

a second locating pin insertable into the second drilled hole of the second bone to locate the second drilled hole, the second locating pin adapted to insert through the second aperture of the drill guide; and the first and second locating pins and the drill guide hold the first bone and the second bone in a retained anatomical position that corresponds with the predetermined anatomical position.

15. The orthopedic fixation system according to claim 11, comprising a depth gauge adapted to determine a depth of the first and second drilled holes to permit selection of an implant with first and second legs having a length corresponding with the depth of the first and second drilled holes.

16. The orthopedic fixation system according to claim 11, comprising a tamp adapted to tamp an implant to an implanted position whereby the first leg resides within the first drilled hole, the second leg resides in the second drilled hole, and the bridge abuts the first bone and the second bone across the fusion site thereof.

17. An orthopedic fixation system for fusing a first bone and a second bone in a predetermined anatomical position, comprising:

a plurality of implants, each implant comprising a first leg and a second leg with a bridge therebetween, whereby:

the first and second legs are spaced apart at a first distance when the implant resides in an unconstrained shape and the first and second legs are spaced apart at a second distance when the implant resides in a constrained insertion shape, each of the first distances for the first and second legs of the implants is different, and each of the second distances for the first and second legs of the implants is different;

a plurality of implant insertion devices, each implant insertion device adapted to constrain one of the plurality of implants in its constrained insertion shape;

a plurality of drill guides, each drill guide including a first aperture and a second aperture therethrough that are spaced apart a preset distance, whereby:

the preset distances between the first and second apertures of the drill guides correspond with the second distance between the first and second legs of one of the plurality of implants in its constrained insertion shape, each drill guide is adapted to reside atop the first bone and the second bone across a fusion site thereof such that the first aperture of the drill guide is located at the first bone and the second aperture of the drill guide is located across the fusion site at the second bone, and the plurality of drill guides provides for a selection therebetween of a drill guide having a correct size;

a plurality of K-wires, whereby:

a first K-wire is adapted to insert through a first aperture of a selected drill guide and into the first bone such that manipulation of the selected drill guide leverages the first bone and the second bone into a conforming anatomical position, whereby the first K-wire and the selected drill guide hold the first bone and the second bone to allow:
a determination of whether the selected drill guide is a correct size in that its preset distance between the first and second apertures spaces apart the first and second apertures across the fusion site of the first bone and the second bone a desired distance for implantation of one of the implants into the first bone and the second bone,
a verification of whether the conforming anatomical position corresponds with the predetermined anatomical position, and
a selection of an implant from the plurality of implants whereby the second distance of the first and second legs for the selected implant corresponds with the preset distance between the first and second apertures of the selected drill guide, and
a second K-wire adapted to insert through a second aperture of the selected drill guide and into the second bone such that the first and second K-wires and the drill guide hold the first bone and the second bone in a retained anatomical position that corresponds with the predetermined anatomical position;
a cannulated drill bit, whereby:
the cannulated drill bit is adapted to fit over the first K-wire and to drill into the first bone until the cannulated drill bit creates a first drilled hole, and
the cannulated drill bit is adapted to fit over the second K-wire and to drill into the second bone until the cannulated drill bit creates a second drilled hole; and
the implant insertion device of the plurality of implant insertion devices constraining the selected implant in its constrained insertion shape is adapted to insert the first leg of the selected implant into the first drilled hole and the second leg of the selected implant into the second drilled hole whereby, after release of the selected implant from the implant insertion device, the selected implant attempts to transition from its constrained insertion shape to its unconstrained shape such that the implant continuously compresses the first bone and the second bone thereby holding the first bone and the second bone in the predetermined anatomical position.

18. The orthopedic fixation system according to claim 17, comprising a plurality of K-wire guides, whereby:
a first K-wire guide is adapted to engage the selected drill guide at its first aperture, the first K-wire guide including a cannulation sized to receive the first K-wire therethrough, whereby the first K-wire guide stabilizes the first K-wire within the first aperture of the selected drill guide; and
a second K-wire guide is adapted to engage the selected drill guide at its second aperture, the second K-wire guide including a cannulation sized to receive the second K-wire therethrough, whereby the second K-wire guide stabilizes the second K-wire within the second aperture of the selected drill guide.

19. The orthopedic fixation system according to claim 17, comprising a sizing guide including a body that defines at a perimeter thereof a plurality of fixed distances corresponding with the preset distance between the first aperture and the second aperture of one of the plurality of drill guides.

20. The orthopedic fixation system according to claim 17, comprising a plurality of locating pins, whereby:

a first locating pin is insertable into the first drilled hole of the first bone to locate the first drilled hole, the first locating pin adapted to insert through the first aperture of the selected drill guide;
a second locating pin is insertable into the second drilled hole of the second bone to locate the second drilled hole, the second locating pin adapted to insert through the second aperture of the selected drill guide; and
the first and second locating pins and the drill guide hold the first bone and the second bone in a retained anatomical position that corresponds with the predetermined anatomical position.

21. The orthopedic fixation system according to claim 17, comprising a depth gauge adapted to determine a depth of the first and second drilled holes to permit selection of an implant from the plurality of implants with first and second legs having a length corresponding with the depth of the first and second drilled holes.

22. The orthopedic fixation system according to claim 17, comprising a tamp adapted to tamp the selected implant to an implanted position whereby the first leg resides within the first drilled hole, the second leg resides in the second drilled hole, and the bridge abuts the first bone and the second bone across the fusion site thereof.

23. An orthopedic fixation system for fusing a first bone and a second bone in a predetermined anatomical position, comprising:
a plurality of implants, each implant comprising a first leg and a second leg with a bridge therebetween, whereby:
the first and second legs are spaced apart at a first distance when the implant resides in an unconstrained shape and the first and second legs are spaced apart at a second distance when the implant resides in a constrained insertion shape,
each of the first distances for the first and second legs of the implants is different, and
each of the second distances for the first and second legs of the implants is different;
a plurality of implant insertion devices, each implant insertion device adapted to constrain one of the plurality of implants in its constrained insertion shape;
a plurality of drill guides, each drill guide including a first aperture and a second aperture therethrough that are spaced apart a preset distance, whereby:
the preset distances between the first and second apertures of the drill guides correspond with the second distance between the first and second legs of one of the plurality of implants in its constrained insertion shape, and
each drill guide is adapted to reside atop the first bone and the second bone across a fusion site thereof such that the first aperture of the drill guide is located at the first bone and the second aperture of the drill guide is located across the fusion site at the second bone;
a sizing guide including a body that defines at a perimeter thereof a plurality of fixed distances corresponding with the second distance between the first leg and the second leg of one of the plurality of implants in its constrained insertion shape, whereby, after manipulation of the first bone and the second bone into a conforming anatomical position, sequential positioning of the fixed distances for the sizing guide across the fusion site of the first bone and the second bone allows:
selection of an implant from the plurality of implants that is a correct size in that its second distance between its first and second legs spaces apart the selected implant across the fusion site of the first bone and the second bone at a desired distance for implantation thereof into the first bone and the second bone, and selection of a drill guide from the plurality of drill guides with a preset distance between its first and second apertures corresponding with the second distance between the first and second legs of the selected implant;

a plurality of K-wires, whereby:
   a first K-wire is adapted to insert through the first aperture of the selected drill guide and into the first bone, and
   a second K-wire is adapted to insert through the second aperture of the selected drill guide and into the second bone such that the first and second K-wires and the drill guide hold the first bone and the second bone in a retained anatomical position that permits a verification of whether the conforming anatomical position corresponds with the predetermined anatomical position;

a cannulated drill bit, whereby:
   the cannulated drill bit is adapted to fit over the first K-wire and to drill into the first bone until the cannulated drill bit creates a first drilled hole, and
   the cannulated drill bit is adapted to fit over the second K-wire and to drill into the second bone until the cannulated drill bit creates a second drilled hole; and the implant insertion device of the plurality of implant insertion devices constraining the selected implant in its constrained insertion shape is adapted to insert the first leg of the selected implant into the first drilled hole and the second leg of the selected implant into the second drilled hole whereby, after release of the selected implant from the implant insertion device, the selected implant attempts to transition from its constrained insertion shape to its unconstrained shape such that the implant continuously compresses the first bone and the second bone thereby holding the first bone and the second bone in the predetermined anatomical position.

24. The orthopedic fixation system according to claim 23, comprising a plurality of K-wire guides, whereby:
   a first K-wire guide is adapted to engage the selected drill guide at its first aperture, the first K-wire guide including a cannulation sized to receive the first K-wire therethrough, whereby the first K-wire guide stabilizes the first K-wire within the first aperture of the selected drill guide; and
   a second K-wire guide is adapted to engage the selected drill guide at its second aperture, the second K-wire guide including a cannulation sized to receive the second K-wire therethrough, whereby the second K-wire guide stabilizes the second K-wire within the second aperture of the selected drill guide.

25. The orthopedic fixation system according to claim 23, comprising a plurality of locating pins, whereby:
   a first locating pin is insertable into the first drilled hole of the first bone to locate the first drilled hole, the first locating pin adapted to insert through the first aperture of the selected drill guide;
   a second locating pin is insertable into the second drilled hole of the second bone to locate the second drilled hole, the second locating pin adapted to insert through the second aperture of the selected drill guide; and
   the first and second locating pins and the drill guide hold the first bone and the second bone in a retained anatomical position that corresponds with the predetermined anatomical position.

26. The orthopedic fixation system according to claim 23, comprising a depth gauge adapted to determine a depth of the first and second drilled holes to permit selection of an implant from the plurality of implants with first and second legs having a length corresponding with the depth of the first and second drilled holes.

27. The orthopedic fixation system according to claim 23, comprising a tamp adapted to tamp the selected implant to an implanted position whereby the first leg resides within the first drilled hole, the second leg resides in the second drilled hole, and the bridge abuts the first bone and the second bone across the fusion site thereof.

* * * * *